US010449026B2

(12) United States Patent
Sostek et al.

(10) Patent No.: US 10,449,026 B2
(45) Date of Patent: Oct. 22, 2019

(54) METHODS AND COMPOSITIONS FOR PROMOTING THE STRUCTURAL INTEGRITY OF SCAFFOLDS FOR TISSUE ENGINEERING

(71) Applicant: Biostage, Inc., Holliston, MA (US)

(72) Inventors: Ron Sostek, Newton, MA (US); David Green, Dover, MA (US); Linghui Meng, Framingham, MA (US); Sherif Soliman, Holliston, MA (US); Joseph Consiglio, Ashland, MA (US)

(73) Assignee: Biostage, Inc., Holliston, MA (US)

( * ) Notice: Subject to any disclaimer, the term of this patent is extended or adjusted under 35 U.S.C. 154(b) by 470 days.

(21) Appl. No.: 13/928,338

(22) Filed: Jun. 26, 2013

(65) Prior Publication Data

US 2014/0141152 A1 May 22, 2014

Related U.S. Application Data

(60) Provisional application No. 61/664,710, filed on Jun. 26, 2012, provisional application No. 61/771,777, (Continued)

(51) Int. Cl.
*A61F 2/06* (2013.01)
*A61F 2/00* (2006.01)
(Continued)

(52) U.S. Cl.
CPC .............. *A61F 2/0063* (2013.01); *A61F 2/02* (2013.01); *A61F 2/04* (2013.01); *A61F 2/07* (2013.01);
(Continued)

(58) Field of Classification Search
CPC .. A61L 27/54; A61L 2400/12; A61L 2420/08; A61L 2430/20; A61L 2300/412;
(Continued)

(56) References Cited

U.S. PATENT DOCUMENTS 5,792,603 A 8/1998 Dunkelman et al.
5,800,537 A 9/1998 Bell
(Continued)

FOREIGN PATENT DOCUMENTS

CN 101372664 A 2/2009
WO WO 2006/099315 A2 9/2006
(Continued)

OTHER PUBLICATIONS

Baede, Towards a new position-controlled electrospinning setup. Jun. 2009.
(Continued)

*Primary Examiner* — Ann Schillinger
(74) *Attorney, Agent, or Firm* — Young Basile Hanlon & MacFarlane, P.C.

(57) ABSTRACT

Aspects of the disclosure relate to synthetic tissue or organ scaffolds and methods and compositions for promoting or maintaining their structural integrity. Aspects of the disclosure are useful to prevent scaffold damage (e.g., delamination) during or after implantation into a host. Aspects of the disclosure are useful to stabilize tissue or organ scaffolds that include electrospun fibers.

16 Claims, 19 Drawing Sheets

Related U.S. Application Data filed on Mar. 1, 2013, provisional application No. 61/786,830, filed on Mar. 15, 2013.

(51) Int. Cl.
*A61L 33/00* (2006.01)
*A61F 2/04* (2013.01)
*A61F 2/07* (2013.01)
*D04H 1/4382* (2012.01)
*D01D 5/00* (2006.01)
*A61L 27/34* (2006.01)
*A61F 2/02* (2006.01)

(52) U.S. Cl.
CPC ............ *A61L 27/34* (2013.01); *D01D 5/0007* (2013.01); *D01D 5/0084* (2013.01); *D04H 1/4382* (2013.01); *A61F 2002/072* (2013.01); *A61F 2210/00* (2013.01); *A61F 2210/0071* (2013.01); *A61F 2210/0076* (2013.01); *A61F 2230/0069* (2013.01); *A61F 2230/0091* (2013.01); *A61F 2240/001* (2013.01); *A61F 2250/0082* (2013.01)

(58) Field of Classification Search
CPC ...... A61L 2430/22; A61L 27/00; A61L 27/28; A61L 27/3625; A61F 2/06; A61F 2/07; A61F 2210/0076; A61F 2002/072; A61F 2/88; A61F 2/04; A61F 2/2418; A61F 2/0077; A61F 2002/821; A61F 2002/828; A61F 2/92
See application file for complete search history.

(56) References Cited

U.S. PATENT DOCUMENTS

| | | | |
|---|---|---|---|
| 5,928,945 A | 7/1999 | Seliktar et al. | |
| 6,121,042 A | 9/2000 | Peterson et al. | |
| 7,348,175 B2 | 3/2008 | Vilendrer et al. | |
| 7,531,503 B2 | 5/2009 | Atala et al. | |
| 7,615,373 B2 * | 11/2009 | Simpson .................. A61F 2/08 435/398 | |
| 8,057,535 B2 * | 11/2011 | Hashi et al. ................. 623/1.43 | |
| 8,507,263 B2 | 8/2013 | Asnaghi et al. | |
| 2002/0182261 A1 | 12/2002 | Dai et al. | |
| 2005/0009178 A1 | 1/2005 | Yost et al. | |
| 2006/0141012 A1 * | 6/2006 | Gingras ........................ 424/442 | |
| 2006/0204539 A1 | 9/2006 | Atala et al. | |
| 2006/0239981 A1 | 10/2006 | Yoo et al. | |
| 2007/0032862 A1 * | 2/2007 | Weber ...................... A61F 2/82 623/1.34 | |
| 2007/0207179 A1 | 9/2007 | Andersen et al. | |
| 2008/0112995 A1 | 5/2008 | Shalev | |
| 2009/0265005 A1 | 10/2009 | Yoo et al. | |
| 2009/0306775 A1 | 12/2009 | Macossay-Torres | |
| 2010/0061962 A1 | 3/2010 | Li | |
| 2010/0129450 A1 | 5/2010 | Atala et al. | |
| 2010/0148404 A1 * | 6/2010 | Smida et al. ................. 264/465 | |
| 2010/0233115 A1 | 9/2010 | Patel | |
| 2010/0292791 A1 * | 11/2010 | Lu .......................... A61K 38/18 623/13.12 |
| 2011/0033918 A1 | 2/2011 | Asnaghi et al. | |
| 2012/0068384 A1 | 3/2012 | Phaneuf et al. | |
| 2012/0135234 A1 | 5/2012 | Netravali et al. | |
| 2012/0271405 A1 | 10/2012 | Soletti et al. | |
| 2012/0330437 A1 | 12/2012 | El-Kurdi et al. | |
| 2013/0041265 A1 | 2/2013 | Sostek et al. | |
| 2013/0177972 A1 | 7/2013 | Green et al. | |
| 2013/0204288 A1 | 8/2013 | Johnson et al. | |
| 2013/0251687 A1 | 9/2013 | Christman et al. | |
| 2014/0107803 A1 * | 4/2014 | Grosse .................. C12M 21/08 623/23.72 |
| 2014/0124670 A1 | 5/2014 | Sostek | |
| 2014/0141152 A1 | 5/2014 | Sostek et al. | |
| 2014/0377848 A1 | 12/2014 | Zink et al. | |
| 2015/0011892 A1 | 1/2015 | Sostek et al. | |
| 2015/0064142 A1 | 3/2015 | Green et al. | |

FOREIGN PATENT DOCUMENTS

| | | |
|---|---|---|
| WO | WO 2006/099333 A2 | 9/2006 |
| WO | WO 2006/113382 A2 | 10/2006 |
| WO | WO 2008/100534 A2 | 8/2008 |
| WO | WO 2013/155488 A2 | 10/2013 |

OTHER PUBLICATIONS

Doshi et al., Electrospinning process and applications of electrospun fibers. J Electrostat. Aug. 1995;35(2-3):151-60. Selected papers from 1993 IEEE Industry Applications Society Meeting Electrostatics in Polymer Processing and Charge Monitoring.

Dzenis, Material science. Spinning continuous fibers for nanotechnology. Science. Jun. 25, 2004;304(5679):1917-9.

Kidane et al., A novel nanocomposite polymer for development of synthetic heart valve leaflets. Acta Biomater. Sep. 2009;5(7):2409-17. doi: 10.1016/j.actbio.2009.02.025. Epub Feb. 21, 2009.

Mironov et al., Bioprinting: directed tissue self-assembly. redOrbit. Jan. 5, 2008. Retrieved from http://www.redorbit.com/news/science/1204166/bioprinting_directed_tissue_selfassembly/ on Jun. 24, 2013. 10 pages.

Prokop, Bioartificial organs in the twenty-first century: nanobiological devices. Ann N Y Acad Sci. Bioartificial organs III: tissue sourcing, immunoisolation, and clinical trials. Nov. 2001;944:472-90. Epub Jan. 25, 2006.

Reneker et al., Nanometre diameter fibres of polymer, produced by electrospinning. Nanotechnol. Sep. 1996;7(3):216-23.

Vasita et al., Nanofibers and their applications in tissue engineering. Int J Nanomedicine. 2006;1(1):15-30.

* cited by examiner

METHODS AND COMPOSITIONS FOR PROMOTING THE STRUCTURAL INTEGRITY OF SCAFFOLDS FOR TISSUE ENGINEERING

RELATED APPLICATIONS

This application claims priority under 35 U.S.C. § 119(e) to U.S. Provisional Application Ser. No. 61/664,710, entitled "METHODS AND COMPOSITIONS FOR PROMOTING THE STRUCTURAL INTEGRITY OF NANOFIBER SCAFFOLDS FOR TISSUE ENGINEERING" filed on Jun. 26, 2012, which is herein incorporated by reference in its entirety. This application claims priority under 35 U.S.C. § 119(e) to U.S. Provisional Application Ser. No. 61/771,777, entitled "METHODS AND COMPOSITIONS FOR PROMOTING THE STRUCTURAL INTEGRITY OF SCAFFOLDS FOR TISSUE ENGINEERING" filed on Mar. 1, 2013, which is herein incorporated by reference in its entirety. This application claims priority under 35 U.S.C. § 119(e) to U.S. Provisional Application Ser. No. 61/786,830, entitled "METHODS AND COMPOSITIONS FOR PROMOTING THE STRUCTURAL INTEGRITY OF SCAFFOLDS FOR TISSUE ENGINEERING" filed on Mar. 15, 2013, which is herein incorporated by reference in its entirety.

BACKGROUND

Tissue engineering can involve generating a synthetic scaffold and seeding the scaffold to produce an engineered tissue that can be implanted into a subject. Different techniques have been used for producing synthetic scaffolds, including nanofiber assembly, casting, printing, physical spraying (e.g., using pumps and syringes), electrospinning, electrospraying, and other techniques for depositing one or more natural or synthetic polymers or fibers to form a scaffold having a suitable shape and size for transplanting into a subject (e.g., a human subject, for example, in need of a tissue or organ transplant).

SUMMARY

In some embodiments, aspects of the disclosure relate to methods and compositions for promoting or maintaining the structural integrity of scaffolds (e.g., synthetic scaffolds) used for tissue engineering. Scaffolds can be used to provide the shape and structural properties of a synthetic tissue or organ. A scaffold can be seeded (e.g., coated) with one or more different cell types prior to implantation into a host (e.g., a human host). A scaffold can be made from synthetic material, natural material (e.g., decellularized tissue or organ material), or a combination thereof. In some embodiments, a scaffold or portion thereof is nanofiber-based, polymer-based, or a combination thereof. Scaffolds can include different components having different structural or surface properties. Different components of a scaffold can provide structural support, flexibility, suitable properties for cell adhesion, etc., or a combination thereof. In some embodiments, different parts of a scaffold can have different shapes, different thicknesses, different surface properties, or a combination thereof. In some embodiments, a scaffold is assembled from different components (e.g., sheets, ribs, etc.) that can be made of the same or different material. Aspects of the present disclosure relate to compositions and techniques for maintaining the structural integrity of a scaffold that includes two or more different components and/or two or more separate layers of material. Methods and compositions described herein can help prevent different components or layers from disassembling (e.g., delaminating) during cellularization or after implantation into a host. Compositions and methods described herein can be used for scaffolds that include one or more components that are made using any suitable technique (e.g., by electrospinning, electrospraying, molding, casting, printing, by lithography, or any combination thereof).

In some embodiments, aspects of the disclosure relate to physical techniques, chemical techniques, or a combination of physical and chemical techniques, that are useful for strengthening tissue scaffolds in order to prevent or reduce damage (e.g., delamination) during cellularization in vitro, during surgical implantation into a recipient, and/or within the recipient after implantation. Accordingly, in some embodiments aspects of the disclosure relate to methods, compositions, and articles that are useful for producing artificial (e.g., synthetic) tissues, organs, or portions thereof that can be implanted into a host (e.g., a human host) to replace diseased or injured tissues, organs, or portions thereof.

In some embodiments, aspects of the disclosure relate to scaffolds that are used for tissue growth. In some embodiments, scaffolds are synthesized having two or more layers of material (e.g., of the same type or of different types) and/or that incorporate one or more additional structures.

In some embodiments, a first layer of electrospun material is deposited on a support that is used for making the scaffold (e.g., a mandrel), and one or more structures (e.g., components that provide structural support within the synthesized scaffold) are applied to the first layer. In some embodiments, a further layer of electrospun material is deposited over the top to produce a synthetic material having one or more structures between two layers of electrospun material. The structure(s) also can be electrospun in some embodiments. However, the structure(s) can be made of any suitable natural or synthetic material. In some embodiments, one or more structures provide structural support for the synthetic scaffold. However, in some embodiments, one or more structures provide functional support (e.g., by providing a channel that allows material to be delivered to the scaffold).

Aspects of the disclosure relate to methods, compositions, and devices that can be used to enhance the structural integrity of scaffolds having two or more layers of material and/or that incorporate one or more additional structures or other components. Aspects of the disclosure relate to methods, compositions, and devices that are useful to improve the mechanical integration of different and/or separate components and/or layers of a synthetic scaffold.

According to some aspects, a device is provided for placing one or more support rings onto a scaffold. In some embodiments, the device comprises a spreader, having a handle, a hinge and a least two support members confronting one another and forming a cavity, each of the support members having a proximal end at the hinge and a distal end, in which the handle and support members are positioned on opposites sides of the hinge, and in which the spreader is configured such that operating the handle causes the at least two support members to rotate in opposite directions about the hinge to manipulate the size of the cavity; at least two spreader blocks fitted at the distal ends of the support members, each of the at least two spreader blocks having a plurality of pockets; and a plurality of rings positioned within the spreader cavity, each ring being inserted into a pocket of the at least two spreader blocks, in which the pockets of the at least two spreader blocks are arranged to align the rings for providing structural support for a synthetic scaffold. In some embodiments, the device further comprises a positioning frame, wherein the at least two spreader blocks are inserted into an opening in the positioning frame. In some embodiments, the device further comprises a pad positioned within the cavity of the spreader adjacent to the hinge and in contact with each ring. In some embodiments, the rings are U or C-shaped structures. In some embodiments, the device further comprises a mandrel passing through the rings within the cavity. In some embodiments, the mandrel is substantially covered with one or more layers of a synthetic scaffold material. In some embodiments, the device is configured as depicted in FIG. 9A.

Scaffolds or portions thereof described herein can be used to generate synthetic organs or tissues or portions thereof, including but not limited to, respiratory tissues (e.g., tracheal, bronchial, esophageal, alveolar, and other pulmonary or respiratory tissues), circulatory tissues (e.g., arterial, venous, capillary, and other cardiovascular tissue, for example, heart chambers of other heart regions or heart or cardiac valves or valve structures), renal tissue (for example renal pyramids of the kidney), liver tissue, cartilaginous tissue (e.g. nasal or auricular), skin tissue, and any other tissue or organ or portion thereof that is being engineered on a synthetic scaffold.

According to some aspects, a method of protecting the structural integrity of a synthetic tissue or organ scaffold is provided. In some embodiments, the method comprises providing a mechanical and/or chemical tether between two or more layers or components of a synthetic tissue or organ scaffold. In some embodiments, two or more layers of the synthetic tissue or organ scaffold are layers of electrospun fibers. In some embodiments, one or more mechanical and/or chemical tethers are introduced during synthesis or assembly of the synthetic tissue or organ scaffold.

Scaffolds generated as described herein can be seeded with appropriate cell types to produce artificial tissues or organs or portions thereof for transplantation into a host.

DETAILED DESCRIPTION

Figure 1A:
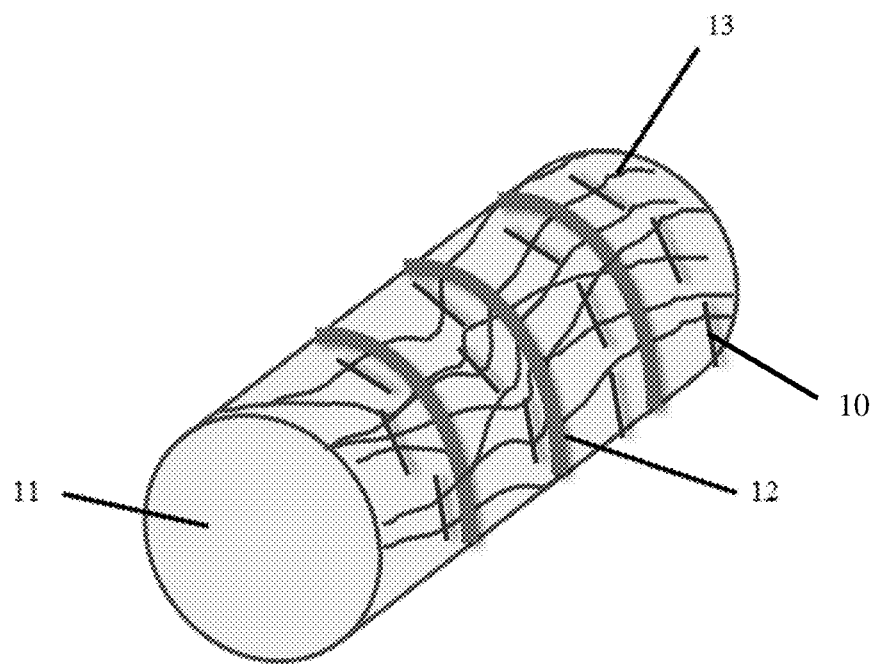
FIG. 1A illustrates a non-limiting example of a tissue scaffold into which a suture pattern has been sewn.

In some embodiments, aspects of the disclosure relate to methods and compositions that are useful for strengthening the connection between two or more regions of a synthetic scaffold that is used for tissue engineering. In some embodiments, a synthetic scaffold may include two or more different components that are assembled to form the scaffold, e.g., prior to cellularization and/or implantation. In some embodiments, a synthetic scaffold includes two or more surfaces that are brought into contact with each other either as a consequence of the final three-dimensional configuration of the scaffold (e.g., due to the presence of folds, etc.), or due to the synthetic techniques that are used to manufacture the scaffold. For example, a scaffold may be synthesized using a technique that involves several steps that result in two or more surfaces being brought together (e.g., the application of a layer of electrospun material onto a portion of the scaffold that was previously made, such as an earlier layer of electrospun material or a surface of a different component that is being incorporated into the scaffold). In some embodiments, aspects of the disclosure relate to methods and compositions for strengthening the connection between different components or regions of a synthetic scaffold, for example where such strengthening enhances the structural integrity of the scaffold.

It should be appreciated that aspects of the disclosure can be used to enhance the structural integrity of different scaffold components having different shapes and sizes (e.g., planar structures such as sheets of material, tubular structures, hollow structures, solid structures, more complex structures, or combinations thereof, any of which can have one or more dimensions ranging from about 1 mm to about 50 cms, for example, or smaller, intermediate, or larger sizes in different directions).

In some embodiments, aspects of the disclosure relate to methods for enhancing the integrity of synthetic organ constructs or natural organ constructs that are produced using electrospun macro or nanofiber material, and/or other synthetic material (e.g., polymeric material, including but not limited to, polyethylene and/or polyurethane based polymers) to provide structural and/or functional components of a tissue scaffold.

In current uses of electrospun materials for scaffolds, problems arise when a second layer of electrospun material is placed on top of first layer that has already been spun. One problem is that the second layer is separate and not physically attached so it can delaminate from the first layer, making the scaffold potentially unstable. This issue also arises when separate components made using other techniques are combined with each other and/or combined with electrospun components of a synthetic scaffold.

Problems arising from the presence of separate (e.g., not physically attached) fibers also can occur for structures that are produced using a technique that involves stopping the electrospinning (for example to place an additional material into the structure) and then restarting the electrospinning (for example to spin over the additional material). Again an unstable condition can exist with the two different electrospun layers being separate and not connected, resulting in potential separation, or delamination, of the two layers. This separation can release the additional material (e.g., a trapped solid entity that was intended to be part of the electrospun structure) and jeopardize the integrity of the entire construct.

In some embodiments, separate or weakly associated regions or layers of fibers can exist even when electrospinning is not stopped. For example, a continuous deposition of fibers can result in separate regions or layers if the pattern of deposition is such that a first region or layer is formed (e.g., electrospun and cured or set) before further fiber is deposited on the first region or layer (for example, if the complexity of the synthesis requires the sequential synthesis of several regions or layers before subsequent regions or layers are added—even if the entire process involves continuous electrospinning).

Different approaches for enhancing the structural integrity of organ and tissue scaffolds (including, for example, electrospun structures) are described herein and illustrated by non-limiting FIGS. 1-11. In some embodiments, methods can include physical or chemical techniques, or a combination thereof. It should be appreciated that each of these techniques can be used alone to reduce the risk of structural failure. However, in some embodiments, one or more of these techniques may be combined as aspects of the invention are not limited in this respect.

Figure 1B:
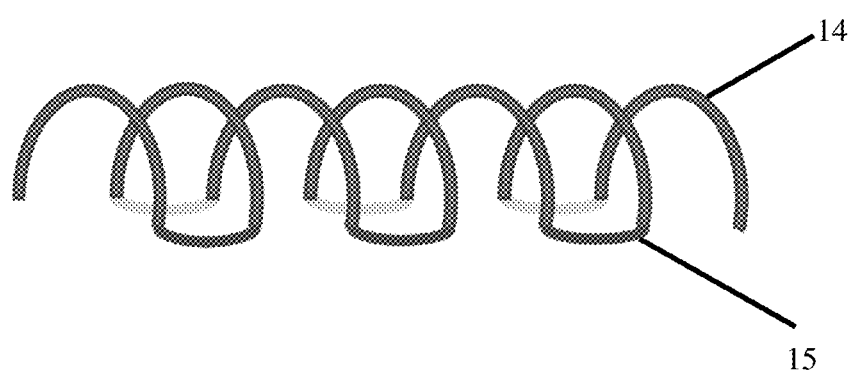
FIG. 1B illustrates a non-limiting example of synthetic tracheal ribs.

In some embodiments, delamination or other structural problems can be reduced by sewing a physical suture into a scaffold as illustrated in FIG. 1. FIG. 1A illustrates sutures (10) in a tubular scaffold (11) that includes support ribs (12) within a scaffold of fibers (e.g., electrospun nanofibers) (13). It should be appreciated that the sutures can be used to strengthen the connection (by providing a physical link) between a surface layer of fibers (shown) and one or more layers of fibers (not shown) beneath the surface layer. It should be appreciated that the pattern of sutures is not limiting and any suitable pattern can be used. In some embodiments, a suture can be used to connect a structural component of a scaffold to a layer of synthetic material (e.g., a layer of polymers or fibers such as a layer of electrospun fibers). FIG. 1B illustrates a non-limiting embodiment of a structural component having a plurality of arcuate (e.g., C-shaped or U-shaped) members (14) connected to each other by connecting members (15) to form a single continuous support component. This component can be used to support a tubular scaffold. However, it should be appreciated that other configurations of a support component can include two or more support features (e.g., each support feature having an arcuate or non-arcuate, for example having an oval, ellipsoid, polygonal, square, rectangular, triangular, etc., frame shape) linked via connecting members of any suitable size or shape (e.g., straight, curved, etc., or any combination thereof) to form a single frame (e.g., a spring-like structure or any other suitable structure). It should be appreciated that in some embodiments, one or more portions of a structural component described herein can be made of a plastic, a metal, or any other material. In some embodiments, a structural component has smooth edges, for example to reduce the risk of damaging adjacent tissue after implantation. In some embodiments, plastic material can be molded, for example injection molded. In some embodiments, metal material can be molded or fabricated. In some embodiments, structural components can be coated (e.g., polymer coated).

Figure 1C:
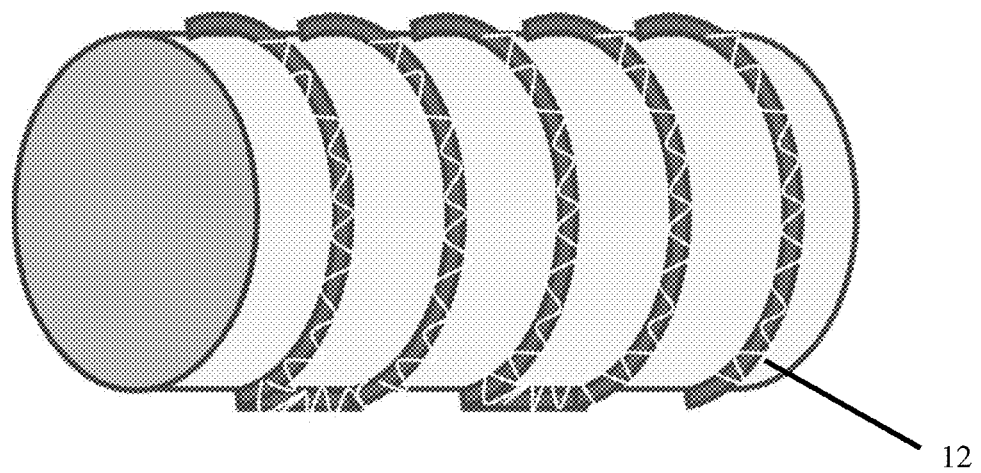
FIG. 1C illustrates a non-limiting example of synthetic tracheal rib sutured into a scaffold.

It should be appreciated that a structural component (e.g., a support structure) can have any suitable shape that provides a framework for supporting other material or parts of a synthetic scaffold. In some embodiments, the size and shape of a support component is designed to support a scaffold for a synthetic tissue or organ of the same or similar size as the tissue or organ being replaced or supplemented in a host (e.g., in a human transplant recipient). In some embodiments, a structural component has an arcuate structure (e.g., similar to the shape of a cartilage ring in an airway, e.g., in a trachea or in an esophagus). In some embodiments, a plurality of structural components are integrated into a synthetic scaffold. In some embodiments, a structural component includes a plurality of arcuate members separated by connecting members, as illustrated in FIG. 1B, to form a single structural component having a plurality of structural members (e.g., arcuate members) that can be used instead of a plurality of structural components that are not connected. It should be appreciated that the structure in FIG. 1B is non-limiting. The structural members (e.g., arcuate members) can have different radii, and can be circular, ovoid, ellipsoid, or other shape in side view. In some embodiments, the structural members can include one or more straight sections and have polygonal shapes in side view. It also should be appreciated that the connecting members can have any size or shape depending on the structural requirements of the scaffold. In some embodiments, the structural component has a spiral, helical, or cork-screw shaped frame that provides continuous structural support without any separate connecting members. FIG. 1C illustrates a non-limiting embodiment of a structural component of FIG. 1B placed on the outer surface of a tubular scaffold layer of a first material (e.g., a first layer of natural and/or synthetic material, for example an electrospun layer of material). In some embodiments, the first layer is a layer of fibers deposited on a mandrel or other collector of an electrospinning device. Non-limiting examples of sutures (12) are illustrated. It should be appreciated that a further scaffold layer (e.g., a second layer of natural and/or synthetic material, for example a second electrospun layer of material) can be deposited on the assembled components illustrated in FIG. 1B. It also should be appreciated that sutures can be used to attached other support components (e.g., other structural elements than can be linear, helical, or any suitable shape as described herein) to one or more layers of synthetic material. A suture can be used to strengthen the connection between separate components and/or layers of a synthetic scaffold. Different types of suture material and suture patterns can be used. In some embodiments, the suture material is biocompatible and/or non-toxic. In some embodiments, the suture material is durable. However, a biodegradable suture material also can be used. It should be appreciated that the suture material can be natural or synthetic. Sutures can be formed from non-absorbable material such as silk, nylon, polypropylene, or other polymers, or cotton, or alternatively sutures can be formed from bio-absorbable material such as, but not limited to, homopolymers and/or copolymers of glycolide, lactide, p-dioxanone and ε-caprolactone. It should be appreciated that a suture can be sewn using an automated technique, or using a robotic technique (e.g., under control of a human operator), or by an individual. In some embodiments, one or more sterile sutures are added under sterile conditions. In some embodiments, a sutured scaffold can be sterilized.

In some embodiments, a scaffold is produced with two or more layers having different percentages of two or more natural or synthetic material (e.g., polymers or fibers). In some embodiments, different gradient percent changes of polymeric material can be used during synthesis. This allows a continuous stream of fiber to be produced with varying polymer concentrations and/or different properties (e.g., different adhesive properties) to produce a continuous fiber that forms the different layers as opposed to the different layers being made from separate fibers (e.g., that are deposited sequentially) that are subsequently connected. In some embodiments, this can help stabilize a scaffold and reduce delamination between different layers. In some embodiments, a mixture of different polymers or polymer percentages can be used to allow for physical properties such as stretching. In some embodiments, stretching can be useful to simulate growth in a synthetic construct. In some embodiments, different percent compositions can include a mixture of absorbable and permanent fibers, for example in a ratio that provides electrical conductivity, provides enhanced or reduced flexibility, allows for increased or reduced stretching, or a combination thereof. In some embodiments, a particular combination of fibers or polymers can be used to represent a predetermined physical state, for example at the time the mixture is spun or at a subsequent time during cellularization or after implantation of the scaffold. In some embodiments, a predetermined physical state can provide one or more physiological cues for biological processes that occur during cellularization or subsequent cell growth or differentiation. In some embodiments, the concentration and/or composition of an electrospun material can be altered by using two or more reservoirs of material (e.g., each reservoir having a different material and/or concentration of material) and altering the relative volume from each reservoir that is deposited during electrospinning. In some embodiments, an electrospinning device having two or more separate nozzles can be used, wherein each nozzle delivers a different material and/or concentration of material. Using such a device, the concentration and/or composition an electrospun material can be altered by altering the volume or material that is deposited from each nozzle at different (e.g., defined) locations on a scaffold being synthesized.

In some embodiments, a solvent (e.g., a low concentration of solvent) or other solution can be applied to one or more components of a scaffold (e.g., sprayed over the scaffold or by soaking the scaffold or by painting certain parts with a brush or a roller) to promote cross linking of fibers to structural support components (e.g., ribs). In some embodiments, the support components (e.g., ribs) can have their surfaces modified. In some embodiments, the surfaces can be softened using solvent. In some embodiments, the surfaces can be produced with a rough or filamentous surface (e.g., by spinning small fibers onto one or more structural components such as synthetic tracheal ribs before assembly of the composite scaffold) that can help strengthen the connection between different layers and components of a scaffold.

Figure 2:
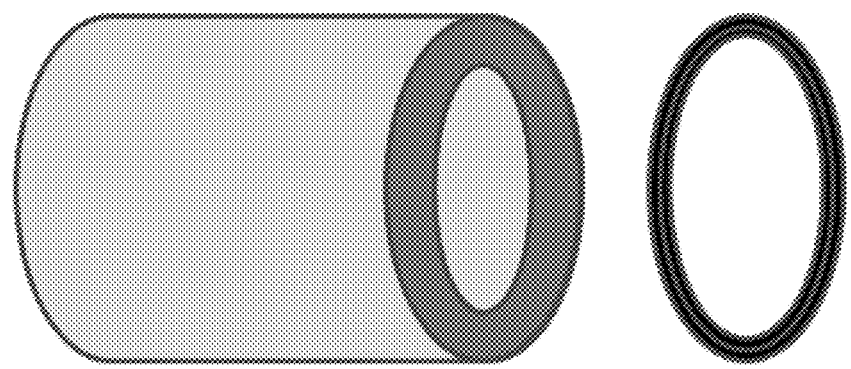
FIG. 2 illustrates a non-limiting example of a tethering structure applied to an end of a tubular tissue scaffold containing layers of fibers to prevent delamination.

In some embodiments, a tethering structure (e.g., a ring or seal) can be applied to one or both ends of a tubular structure (or other structure) containing two or more layers of fibers (e.g., nanofibers) to prevent delamination, as illustrated in FIG. 2. In some embodiments, the tethering structure physically holds the edges or ends, or portions thereof, of two or more layers of synthetic material together. In some embodiments, the tethering structure can have clips, ridges, slots, or other physical features that can be used to physically attach to an edge, end, or portion thereof, of one or more layers (e.g., 2 or more) of synthetic material, or one or more other scaffold components, or a combination thereof. The tethering structure can be of any suitable material, including, but not limited to, metal, plastic, other polymeric material, or any combination thereof. In some embodiments, the tethering structure is autoclavable.

In some embodiments, one or more tethering structures can be used to mechanically associate two or more layers or different components of a scaffold by penetrating the two or more layers (e.g., crossing through the two or more layers) and having a fastening feature (e.g., a broader member or cap that can be placed at either end of a thinner penetrating member) to keep the layers together. In some embodiments, tethering structures can be rivets, snaps, buttons, grommets, staples or pins or other structures that can penetrates two or more layers and mechanically connect them. In some embodiments, a plurality of tethering members may be used to mechanically stabilize to or more layers of material (e.g., electrospun material). In some embodiments, a surface (e.g., an end surface of the broader member or cap) of a tethering structure has one or more physical or chemical features (e.g., it is etched, porous, has another physical surface property that is compatible with cell growth and/or is coated with one or more growth factors) if it will be exposed on a surface of a scaffold that is to be cellularized. In some embodiments, a surface (e.g., an end surface) of a tethering structure is shaped to avoid sharp edges or other features that could damage the scaffold or surrounding tissue after implantation.

Figure 3:
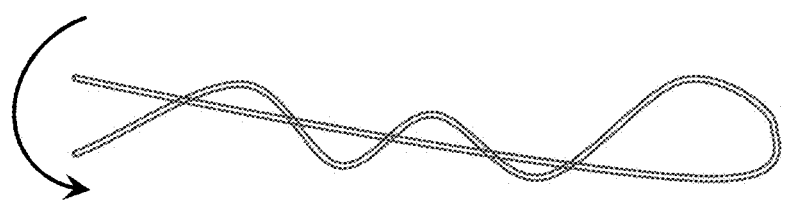
FIG. 3 illustrates a non-limiting example of tissue scaffold fibers twisted or tied together to provide mechanical integration between the fibers.

In some embodiments, fibers that are not covalently connected can be twisted or tied (e.g., as illustrated in FIG. 3) to strengthen their connection or association within a scaffold. In some embodiments, the twisting or tying can be performed at set intervals during synthesis. In some embodiments, the twisting or tying can form a knot-like structure that can help hold separate fiber strands together. Other methods for connecting fibers to strengthen their connection or association within a scaffold are disclosed herein.

In some embodiments, different layers of fibers can be interwoven by interweaving one or more fibers during synthesis to increase the mechanical integration between different regions of a scaffold. In some embodiments, a collector (e.g., a mandrel) and or one or more nozzles that are used in an electrospinning process can be mounted on a pivot or other movable support (e.g., a robotic arm) that can be used to control the relative orientation of the collector and the nozzle(s). By altering the relative orientation of the collector and nozzle(s) during electrospinning (e.g., in x, y, and/or z planes) a proportion of the polymers being deposited can be interwover or entangled thereby providing increased mechanical integration. In some embodiments, an increase of 1% or more (e.g., 5%, 10%, 25%, or more) of the extent of fiber entanglement can lead to improved structural stability.

Figure 4:
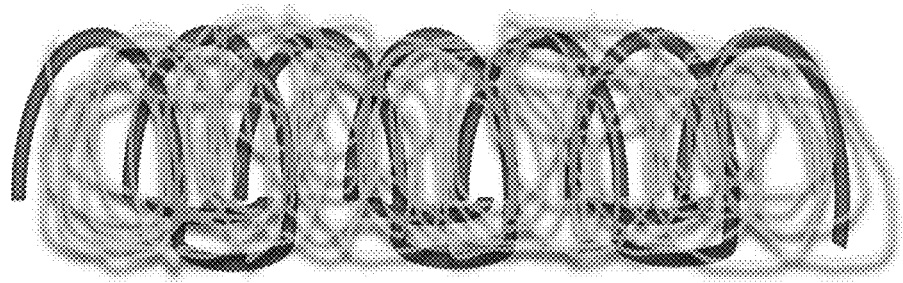
FIG. 4 illustrates a non-limiting example of a single continuous structural component incorporated into two or more electrospun layers.

In some embodiments, one or more structural components are inserted within an electrospun fiber material. For example, a continuous structural component that spans a length of a scaffold can be inserted within an electrospun nanofiber material. In some embodiments, the continuous element can be incorporated (e.g., captured by electrospinning) into two or more layers or regions (e.g., formed by electrospun fibers that are not connected). It should be appreciated that the continuous element can have any suitable shape (e.g., a coiled or approximately coiled shape as shown in FIG. 4 or any other shape as described herein). A continuous structural element can be generally elongate (e.g., long and thin, for example in the form of a string, fiber, tape or similar structure) and shaped to match the general 2 or 3 dimensional shape or contours of the synthetic material it is intended to support. However, the structural element can have other shapes including portions that are in the forms of discs or sheets or other more complex shapes. A structural element can be made of any suitable material, including, but not limited to, a metal, a plastic, a natural material, a fiber (e.g., an electrospun fiber), any suitable polymer, or any other material, or any combination thereof (e.g., a coated material, such as a metal coated with a plastic, resin, and/or other polymer). In some embodiments, a structural element is autoclavable. Typically, a structural component is more rigid or less elastic or compliant than a non-structural component of a scaffold. In some embodiments, a structural component is made of the same material as a non-structural component, but is thicker in one or more dimensions than the non-structural component. For example, the non-structural component may be a sheet whereas a structural component may be a linear and/or arcuate support structure that is thicker than the sheet (for example, a rib of an airway scaffold). In some embodiments, a structural component is made of or includes one or more different materials than the non-structural component. It should be appreciated that the reference to structural and non-structural components indicates that a function of the structural component is to provide support for one or more non-structural components. Non-structural components can nonetheless contribute to the structural stability of a scaffold, and can also serve a structural role of providing support for cellularization for example.

In some embodiments, one or more structural components (e.g., a continuous support structure) provide a backbone that can be shaped to support a tubular structure (see FIG. 4 for example), for example a tubular scaffold that is used to produce a synthetic airway. As used herein, the term "tubular" or "tube-shaped" refers to objects having cavities with any cross-sectional shape, including for example and not limited to rounded shapes (e.g., oval, circular or conical), quadrilateral shapes, regular polygonal or irregular polygonal shapes, or any other suitable shape. Accordingly, this term is not intended to be limited to the generally circular cross-sectional profile of the exemplary tubular cavities illustrated in certain figures.

In some embodiments, one or more structural components (e.g., a continuous support structure, for example a synthetic framework or backbone or a plurality of rings or other structural components as described herein) can be incorporated into a micro or nanofiber structure to create a tubular structure that can have the shape of a trachea and be used as a basis for a tracheal implant. However, one or more structural components (e.g., a continuous support structure) can have any appropriate shape and can form the backbone of an electrospun structure for other organs. In some embodiments, a continuous component provides greater support and tissue integrity than a plurality of separate supports (e.g., rings or ribs) that are not connected to each other. In some embodiments, one or more structural components illustrated in FIG. 1 or FIG. 5 can be clipped over a tubular scaffold (e.g., a first layer of electrospun material on a collector such as a mandrel). In some embodiments, the structural component can be attached to the first layer using a technique described herein and/or a second layer of material can be electrospun over it to form a composite scaffold.

In some embodiments, one or more structural components (e.g., a continuous support structure, for example, a coiled backbone) can be electrically conductive, non-electrically conductive, or include a combination of conductive and non-conductive portions. In some embodiments, the continuous support component (e.g., coiled backbone) can be a metallic or polymeric structure. In some embodiments, the continuous support structure (e.g., coiled backbone) can be made up of multiple materials. In some embodiments, the continuous support structure (e.g., coiled backbone) can include coated and/or non-coated portions.

In some embodiments, an electrically conductive support component (e.g., coiled backbone) is an integral part of an electrospun macro or nanofiber tubular synthetic organ structure (e.g., vessel, airway, for example an esophagus or trachea, or gut, for example a stomach or intestine, etc., or any portion thereof). In some embodiments, the continuous support component (e.g., coiled backbone) is selectively electrically charged (e.g., during synthesis of the scaffold, for example, during electrospinning). In some embodiments, the charge is positive, negative, alternating, biphasic, pulsed, ramped, etc., or a combination thereof. In some embodiments, the amplitude and profile of an electric charge or current on one or more portions of a conductive support component can be adjusted or programmed (e.g., using a controller connected to a computer). In some embodiments, the charge is selectively controlled and/or maintained in order to alter the bonding properties of electrospun macro or nanofiber layers which come into contact with the support component (e.g., backbone). In some embodiments, the purpose of this selective control is to improve binding of electrospun fibers to the support component and thereby reduce the likelihood (e.g., through bonding) of delamination of electro spun nanofiber layers deposited on an organ or tissue scaffold (e.g., a tubular synthetic organ scaffold).

In some embodiments, the continuous support structure (e.g., coiled backbone) is an electrically conductive backbone that serves as the electrospinning mandrel for the purpose of creating an electrospun nanofiber scaffold (tubular synthetic organ structure) on the conductive structural element. However, it should be appreciated that in this context, the conductive structural element is retained within the scaffold (unlike a mandrel that is removed after the scaffold is formed on the mandrel via electrospinning). In some embodiments, the electrical characteristics of the structural component (e.g., backbone) are tuned to control the deposition of electrospun nanofibers anywhere along the entire dimension of the tubular synthetic organ scaffold. In some embodiments, the electrical characteristics of the structural component (e.g., backbone) are tuned to provide deposition of electrospun macro or nanofibers which can be uniform, differential, alternating, mixed, aligned, non-aligned etc. In some embodiments, the deposition is utilized to create an electrospun nanofiber tubular synthetic organ structure with specific mechanical or biological properties including: tensile strength, rotation, compression, range of motion, bending, resistance, compliance, degrees of freedom, gas permeability, pore size, cellular engraftment, differentiation, proliferation, infiltration, angiogenesis, vascularization, etc., or any combination thereof.

In some embodiments, aspects of the invention relate to an electrospun nanofiber tubular synthetic organ structure having one or more structural components (e.g., a continuous support component, for example, a coiled backbone, or two or more structural rings or ribs, etc.) that each possess integrated micro and/or nano features that can combine (e.g., attach to) with complementary counterpart micro and/or nano features of the electrospun nanofiber layers that are contacted, thereby enhancing the bonding properties between the one or more structural components and the electrospun fibers (e.g., nanofibers). In some embodiments, one or more layers may include a layer of electrospun nanofibers below a structural component (e.g., a coiled backbone), above it, or both below and above. These layers can possess complementary counterpart micro and/or nano features to those possessed by the coiled backbone. In some embodiments, the complementary counterpart micro and/or nano features are of a hook and loop configuration. In some embodiments, the complementary counterpart micro and/or nano features are of a tab and slot configuration, a ball and socket configuration, a tongue and groove configuration, or any other complementary structural configuration as aspects of the invention are not limited in this respect.

In some embodiments, aspects of the invention relate to an electrospun nanofiber tubular synthetic organ structure comprising one or more support components (e.g., a coiled backbone) that possesses integrated micro and/or nano features that can anchor, attach, or bind to the electrospun macro or nanofiber layer(s) they contact. In some embodiments, the layers can include a layer of electrospun macro or nanofibers on a first side of a support component (e.g., the coiled backbone), a second side of the support component, or both. In some embodiments, the layers themselves act as permissive substrates for the anchoring, attachment, or binding of the support component (e.g., coiled backbone) they contact.

In some embodiments, aspects of the invention relate to an electrospun nanofiber tubular synthetic organ structure constructed using a single continuous electrospun nanofiber (as opposed to using separate nanofibers) in order to promote structural integrity. In some embodiments, a separate support component is incorporated into the organ structure. In some embodiments, the support component is incorporated during electrospinning without stopping the electrospinning process (thereby maintaining a single continuous fiber which reduces the problem of delamination). In some embodiments, the electrospinning process is slowed rather than stopped. In some embodiments, the process is slowed using a concerted software control of two or more (e.g., all) adjustable electrospinning parameters and the location (e.g., rotational position on the support) and/or timing of the change in speed can be triggered by an encoder on the rotating motor (e.g., mandrel motor) to allow the exact position (e.g., rotational position) of the support (e.g., mandrel) to be identifiable, and, in some embodiments, communicated to the software. In some embodiments, the purpose of slowing the electrospinning process is to allow a software controlled robot to place one or more support structures (e.g., backbone elements) onto a partially completed electrospun nanofiber tubular synthetic organ structure. In some embodiments, this placement is facilitated by using an encoder. In some embodiments, an encoder can be an electrical device and/or an electrically detectable device that is placed at one or more defined positions on a mandrel. In some embodiments, an encoder can be a physical or optically detectable feature (e.g., a protrusion, or other physical feature, or a reflective material, a barcode, a color, or other optically detectable feature) that is located at one or more positions on a collector (e.g., a mandrel). In some embodiments, an encoder is an RFID device. It should be appreciated that the encoder should be located on the collector (e.g., mandrel) at a position that does not interfere with detection when one or more scaffold layers are on the collector. In some embodiments, an encoder is placed at one or both ends of a collector in an area that is not covered by a polymer during synthesis. However, in some embodiments, an encoded can be placed under an area that will be covered by polymer if the signal from the encoder can still be detected.

In some embodiments, the construction process is facilitated by using an electrospinning mandrel to tune the mechanical and biological properties of the electrospun nanofiber tubular synthetic organ structure, obviating the need for the insertion of one or more backbone elements.

In some embodiments, aspects of the invention relate to using simultaneous multi-fiber (e.g., 2 fiber) electrospinning with dense fibers (e.g., PET fibers) used for support components (e.g., ribs of a tracheal scaffold) and more elastic fibers (e.g., PU or blended PET/PU) for spaces between the support components. In some embodiments, support components (e.g., ribs) are made by oscillating back and forth the angular rotation of the mandrel (e.g., approximately 270 degrees, however other angles may be used) during deposition of the fiber. In some embodiments, as many syringe nozzles as ribs (e.g., between 6 and 10, or more or less) may be used. In some embodiments, one or more nozzles can be moved stepwise along the longitudinal axis of a mandrel. In some embodiments, after a small mass of rib material is built up (e.g., between one hundredth and one fifth of total rib mass) for one or more ribs (e.g., all ribs), the posterior wall of the scaffold and the inter rib spaces can be covered in a layer of more elastic material (e.g., a blend of between 100% PU and 50% PU/50% PET). This process of delivering a structural component by spinning or by depositing a polymer (e.g., biological or inorganic) provides the ability to deliver the component and cure with a curing stimulant (e.g., light or heat) to improve the structural integrity of the resulting scaffold. In some embodiments, a plurality of layers can be applied. In some embodiments, the fibers at each level can be attached to or incorporated into a polymer feature. Accordingly, a scaffold spun material can be embedded into the structural feature thereby reducing or eliminating delamination of the fibers. This process can be used to produce a scaffold made of a single mass of fibers, thereby reducing the delamination between layers of materials used in current scaffolds, while maintaining a radially strong but longitudinally flexible tracheal scaffold.

It should be appreciated that this technique also could be used for other organs, particularly tubular organs, for example the gastro-intestinal tract, and for other organs requiring scaffolds with varying mechanical properties (e.g., heart, bone, liver, or kidney). In some embodiments, the same technique can be used with longitudinal ribs rather than radial ribs, for example for esophageal scaffold construction. In some embodiments, this technique can be used to differentiate fibers into horizontal and vertical designs, for example to simulate natural tissues (e.g., smooth or striated or slanted or bundled). In some embodiments, these designs can serve as cues (e.g., simulating biological cues) for the cells being deposited to properly differentiate. In some embodiments, these designs are useful to stabilize a synthetic construct.

In some embodiments, in order to obtain fibers having appropriate structural properties (e.g., flexibility and/or elasticity), the fibers can be exercised (e.g., exposed to repeated flexing, twisting, extending, and/or compressing) to increase the compliance of the fiber material (e.g., so that stiff materials become compliant). In some embodiments, the fibers can be exercised during synthesis of a scaffold component (e.g., structural element) or other synthetic material. In some embodiments, a scaffold component or other synthetic material can be designed and/or produced to have a restricted bending radius (e.g., using an exterior shielding for example with a desired bend radius or anchor stich to limit the flexibility of the polymer). This can be useful, for example, to allow for a desired flexibility or other structural property to be imparted to a material during synthesis, but wherein the flexibility or other structural property does not change subsequently or during use (e.g., after it is incorporated into a synthetic scaffold). In some embodiments, excerising involves exposing a scaffold element to repeated horizontal and/or vertical forces that do not exceed the breaking point of the polymer (or other scaffold material). In some embodiments, a restricted bend radius can be useful for scaffolds that are used for hollow tissue and/or solid tissue (e.g., airways, lungs, veins, heart, heart valve, liver, kidney, etc.) or portions thereof.

In some embodiments, the structural integrity of a scaffold can be improved by combining different components that have compatible (e.g., similar or identical) flexibilities and/or other physical properties that also are compatible with the structural or physical requirements in the host after implantation. In some embodiments, a technique of exercising synthetic fibers to obtain a desired fiber characteristic can be useful to protect the integrity of a scaffold by providing elements having sufficient structural flexibility (e.g., even when using natural ridged materials). This technique also can be used to modify the properties of certain polymers or other materials that are acceptable for use in a subject (e.g., physiologically acceptable and/or approved by a regulatory agency) even if the polymers or other materials do not inherently have the appropriate flexibility or other physical property that may be desired for use in a synthetic organ or tissue scaffold. In some embodiments, a desirable level of flexibility can be based on structural properties that are important for an engineered tissue or organ after implantation into a recipient. In some embodiments, a target level of flexibility can be obtained by exercising synthetic fibers, measuring the resulting flexibility, and repeating the exercising and measuring steps if necessary until a desired level of flexibility is obtained. In some embodiments, the physical properties (e.g., flexibility) of two or more different components in a synthetic scaffold can be matched (e.g., to be within 0-25%, for example about 0-5%, 5-10%, 10-15%, 15-20%, or about 20-25% of each other) in order to reduce or avoid delamination or other structural failure of an engineered tissue or organ due to different components of the scaffold having different physical properties (e.g., different flexibilities).

In some embodiments, a scaffold material may be exercised to impart sufficient flexibility to allow for expansion or stretching (e.g., to allow for growth of a synthetic tissue or organ after implantation). In some embodiments, a synthetic organ or tissue may expand in response to one or more internal cues provided by the body of a host and/or one or more external cues or stimuli (e.g., electrical and/or pressure cues, and/or other external cues).

In some embodiments, one or more structural components (e.g., ribs or other support structures) can be molded, and fibers can be spun or woven around the component(s). In some embodiments, the structural component(s) include small anchors (e.g., filamentous, fibrous, or hair-like anchors, for example having a diameter of several 1-5 nm and a length of 5-50 nm, however other sizes also can be used for example larger or smaller diameters or lengths) that help connect the structures to the electrospun or woven material.

In some embodiments, a heated mandrel can be used to melt (e.g., partially melt) one or more layers of fibers that are electrospun thereby promoting their connection by fusing them. In some embodiments, this technique can be used to reduce subsequent delamination of different fibers. In some embodiments, a heat source can be used to melt (e.g., partially melt) regions of one or more scaffold components (regardless of how they are made) during or after their assembly to form the scaffold. This also can be useful to reduce subsequent disassociation (e.g., delamination) of separate scaffold components.

Figure 5A:
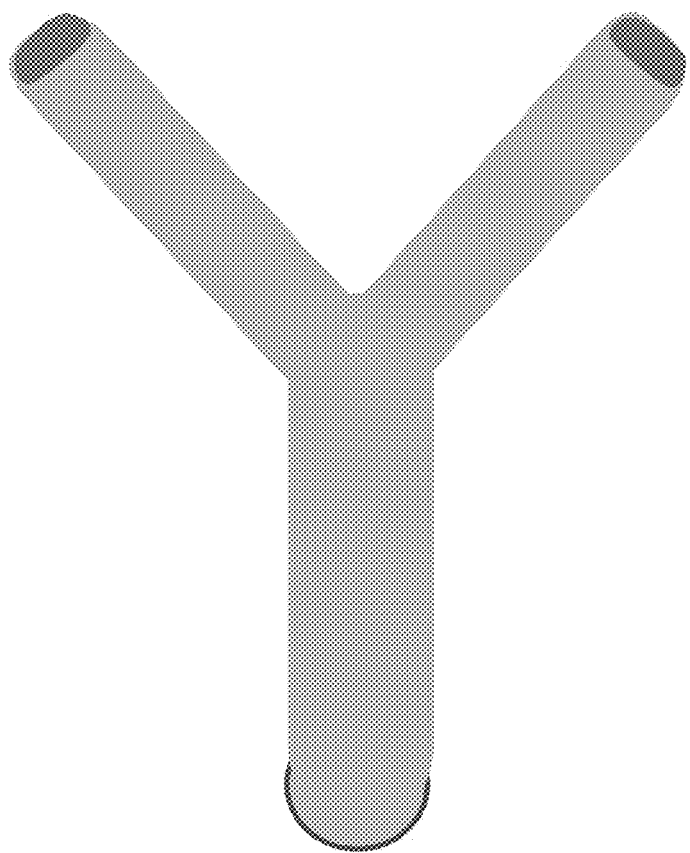
FIG. 5A illustrates a non-limiting example of a branched mandrel that can be used to form a scaffold.
Figure 5B:
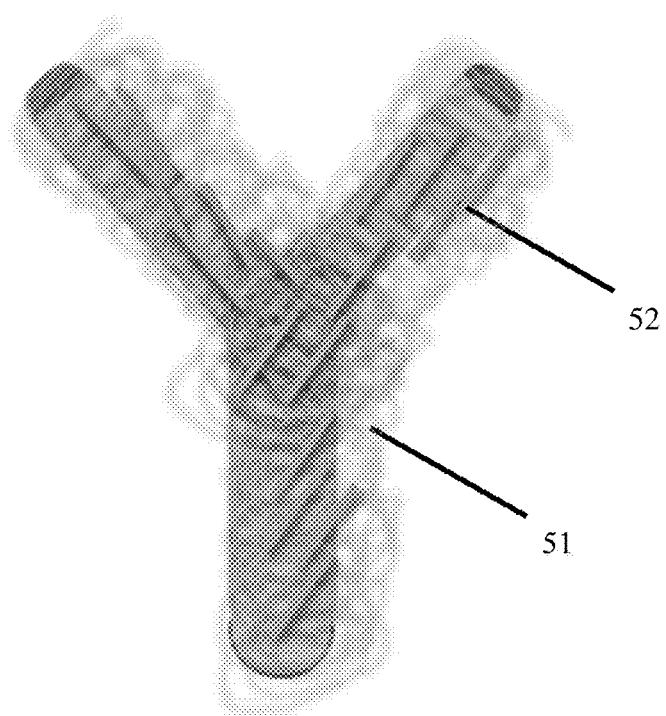
FIG. 5B illustrates a non-limiting example of two different types of fiber deposited on a synthetic support.

In some embodiments, two or more streams of fibers are provided (e.g., during an electrospinning process). In some embodiments, a first stream is continuous and a second stream is intermittent (e.g., spitting small fibers). This is illustrated in FIG. 5. FIG. 5A illustrates an example of a branched structure that can be used to form a scaffold. The branched structure can be a branched mandrel or other collector that can be used for electrospinning to deposit one or more fibers. FIG. 5B illustrates two different types of fiber (51, 52) that were deposited on the branched structure of FIG. 5A.

Figure 5C:
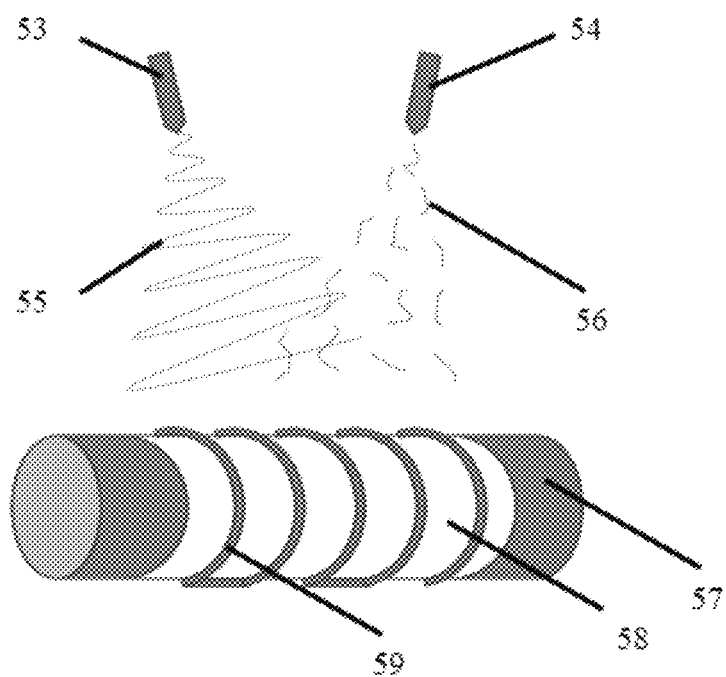
FIG. 5C illustrates a non-limiting example of two streams of fiber being deposited via electrospinning from two nozzles.

FIG. 5C illustrates a non-limiting embodiment of a technique for depositing two different types of fiber using two nozzles. In some embodiments, fibers deposited in a second stream can provide different adhesive or structural properties that can be incorporated into the fiber being deposited by a first stream. FIG. 5C illustrates a continuous and an intermittent stream. However, it should be appreciated that two continuous streams of different material or two intermittent streams of different material also can be used. By combining the two fibers during synthesis, subsequent separation or delamination can be reduced. In some embodiments, three or more (e.g., 3-5, 5-10, or 10-15 or more) different streams can be used (e.g., including any combination of intermittent and continuous streams of different material). It should be appreciated that 2 or more different streams can be deposited simultaneously (or sequentially or a combination thereof) using an electrospinning device that includes 2 or more nozzles each independently controlled and connected to different reservoirs of material. FIG. 5C illustrates a non-limiting embodiment of two streams of fiber (55, 56), one of which is intermittent (producing, for example, shorter fibers), being deposited via electrospinning from two nozzles (53, 54). The fibers are illustrated as being deposited onto a scaffold support component (59) that is placed on a first scaffold layer (58) that was previously deposited on a mandrel (57). It should be appreciated that the first scaffold layer also can be produced using a single stream of material or a combination of two or more different streams of material (e.g., from two or more different nozzles). In some embodiments, co-electrospinning with short fibers (e.g., using an intermittent stream) can increase the mechanical strength of a scaffold. In some embodiments, short polymer fibers can create connections between longer electrospun fibers. In some embodiments, shorter fibers can physically intertwine longer electrospun fibers (e.g., in a tracheal scaffold) so that the resulting scaffold has fewer separate layers and the layers are mechanically connected to form a thicker layer. In some embodiments, the shorter fibers can be wet fibers to increase the adhesion between the fibers, and/or between the fibers and structural components (e.g., ribs in a tracheal scaffold).

Figure 5D:
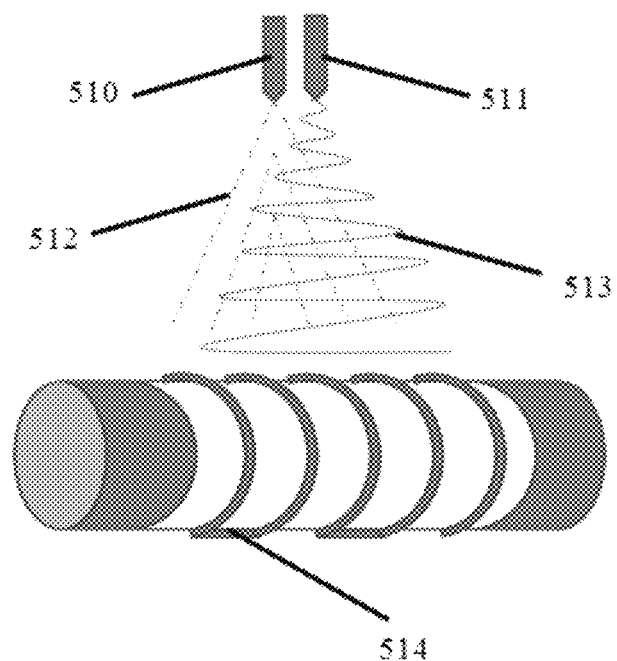
FIG. 5D illustrates a non-limiting example of a nozzle depositing an electrospun material and another nozzle delivering a solvent or other material that promotes adhesion of the electrospun material to a support component of a synthetic tissue scaffold.

In some embodiments, delamination of different components of a scaffold can be reduced or avoided by applying a material that promotes adhesion or coherence between the different components (e.g., during synthesis). FIG. 5D illustrates a non-limiting example where one of two nozzles (511) deposits an electrospun material (513) (e.g., fiber, for example a nanofiber) and the other nozzle (510) delivers a solvent (512) or other material (e.g., an adhesive or cross-linker) that promotes adhesion of the electrospun material to the support component (514). However, it should be appreciated that other techniques can be used to apply a solvent or other material to promote adhesion between two or more separate layers or components of a tissue or organ scaffold. In some embodiments, a structural component (e.g., a frame for example as illustrated in FIG. 1) is coated with one or more solvents prior to being placed on a scaffold, for example prior to being snapped onto a first scaffold layer. In some embodiments, a solvent can be sprayed on (e.g., electrosprayed). In some embodiments, the structural component, or a portion thereof (for example the portion that is going to contact another scaffold component) can be dipped in solvent or otherwise coated with solvent prior to being added to a scaffold during assembly. The coated solvent helps fibers stick to the structural component(s) (e.g., ribs) and may create chemical and/or physical bonds between different components of a scaffold.

Figure 6A:
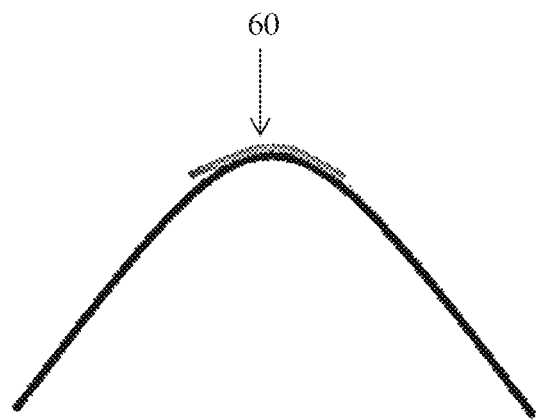
FIG. 6A illustrates a non-limiting example of a solution that is applied to a portion of the surface of a first synthetic element.
Figure 6B:
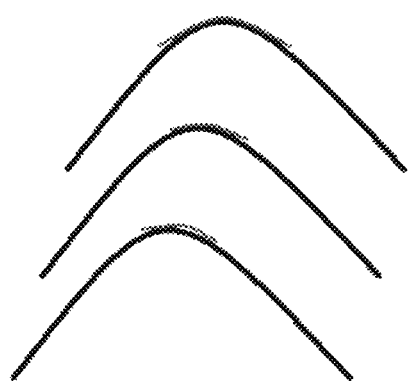
FIG. 6B illustrates a non-limiting example of a solution applied to a portion of several synthetic elements.
Figure 6C:
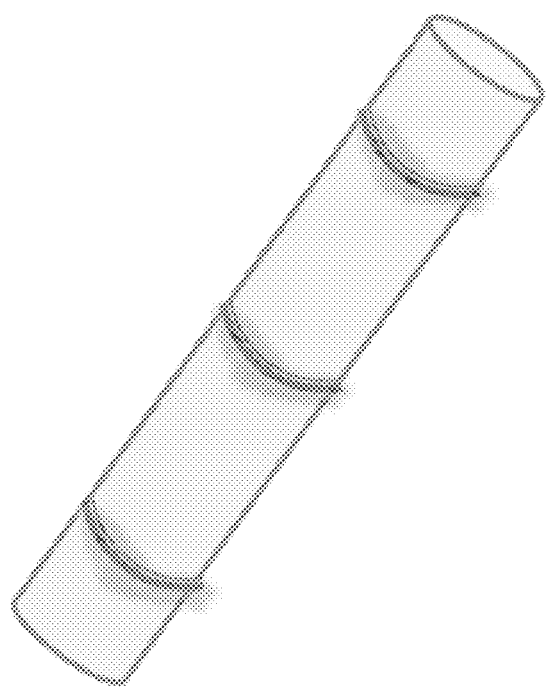
FIG. 6C illustrates a non-limiting example of three structural components placed on a cylindrical support.

In some embodiments, a solution may be applied to a portion of a surface of a first synthetic material in order to promote adhesion between that portion of the first synthetic material and a portion of a second synthetic material that is applied or contacted to the first material. FIG. 6 illustrates a non-limiting embodiment of a solution applied to one or more surfaces of a first synthetic material. FIG. 6A shows a non-limiting embodiment of a solution 60 that is applied to a portion of the surface of a first synthetic element. FIG. 6B illustrates the solution applied to a portion of several synthetic elements. Each synthetic element can be a structural support component (e.g., an artificial cartilage ring that is made of synthetic and/or natural material). The solution can help promote adhesion of a second material to the first material. In some embodiments, the first material is a structural component placed on a support (e.g., a mandrel) and the second material is a fiber that is electrospun onto the first material. In some embodiments, the structural component is placed directly on the mandrel. However, in some embodiments, an initial layer of electrospun material is deposited on the mandrel prior to the structural component. As a result, application of the second material over the structural components produces a multi-layered scaffold having one or more structural components placed between two layers of electrospun material. It should be appreciated that the two layers on either side of the structural components can include the same types of electrospun fibers or different types of electrospun fibers. FIG. 6C illustrates a non-limiting embodiment of three structural components placed on a cylindrical support (e.g., on a first layer of electro spun material on the cylindrical support), wherein at least a portion of each structural component is coated with the solution. The solution can promote adhesion of the fibers to the structural components (e.g., the fibers stick preferentially to the first material as the fibers pass over the region that is coated with a solution during electrospinning). It should be appreciated that a solution also could be applied to the first layer (or regions of the first layer) of material before the structural components are placed or electrospun on it in order to promote adhesion or prevent subsequent delamination. In some embodiments, the resulting scaffold can be an airway scaffold (e.g., an esophageal or tracheal scaffold) or a portion thereof, or a portion of a tubular region of a scaffold for another tissue or organ. However, it should be appreciated that similar techniques can be used for other organs.

In some embodiments, the first synthetic material may be a structure, for example a support structure, that is being incorporated into a scaffold for a synthetic organ or tissue. In some embodiments, the structure is a rib on a tracheal scaffold. However, the structure may be any structure (e.g., any support structure) that is being incorporated into a scaffold for any synthetic organ or tissue. In some embodiments, the second material is an electrospun material that is being deposited onto the first material (e.g., the support structure). However, techniques described herein may be used for any material being incorporated into a synthetic scaffold as aspects of the disclosure are not limited to electrospun nanofiber-based scaffolds.

In some embodiments, a solution, suspension, gel, cream, powder, or combination thereof, can be applied to the surface of a first scaffold component in order to promote adhesion or other form of physical attachment to a second scaffold component. In some embodiments, a solution is an aqueous solution that is useful to promote adhesion between the first and second material. In some embodiments, the solution is a solvent or adhesive (e.g., a biologically compatible solvent or adhesive). In some embodiments, the solution is hexafluoroisopropanol or chloroform. In some embodiments, the solution contains one or more cross-linkers. In some embodiments, the solution is capable of solubilizing one or more components of the first and/or the second material. It also should be appreciated that a gel or paste having similar properties also may be used as aspects of the disclosure are not limited in this respect. In some embodiments, a curing polymer (e.g., a solution of curing polymer) can be used. Any suitable polymer can be used (e.g., polyethylene, nylon, a biopolymer, etc.). Curing can involve any suitable technique including UV exposure, heat, or other technique.

The solution may be applied using any suitable technique, including spraying, painting, depositing using one or more rollers or pads, or any other technique that can be used to deposit the solution on the first material (e.g., structure).

In some embodiments, one or more sprayers or other delivery devices can be used to deposit one or more structural elements (e.g., one or more rings on a synthetic airway). In some embodiments, the same or separate sprayer(s) can be used to deposit a curing polymer at appropriate positions. In some embodiments, an encoder or other device that provides information about the rotational position of a mandrel can be used to guide the sprayers to deposit different materials in the correct location and order on a support (e.g., on a mandrel).

In some embodiments, the solution is applied during rotation of an electrospinning device. For example, a support structure placed on a mandrel may be rotating and a solution (e.g., a solvent) may be applied to predefined portions of the rotating support structure prior to depositing an electrospun nanofiber onto the support structure. In some embodiments, the pattern or location of deposition of the solution onto a rotating support structure can be determined by synchronizing the deposition process with the rotation of the mandrel (e.g., using a mark or register on the mandrel that controls the timing of deposition). However, it should be appreciated that the solution can be applied to a support structure that is not in motion (e.g., not spinning). This technique also can be used in conjunction with any synthetic structure and is not limited to a support structure on a mandrel.

In some embodiments, a solution may be applied to the entire surface of a structure (e.g., a support structure) in order to promote adhesion with a second material. However, in some embodiments, the solution is applied only to a portion of the structure (for example, as illustrated in FIG. 6) to promote preferential adhesion of the second material to one or more defined regions of the structure. Accordingly, these techniques can be used to enhance the attachment strength between different materials in a synthetic scaffold that is used for organ or tissue engineering. It should be appreciated that in some embodiments, a gel, suspension, cream, powder, or combination thereof, or other form of material can be used to promote adhesion or physical attachment instead of or in addition to a solution.

In some embodiments, instead of, or in addition to, applying a separate solution between different scaffold components, either or both of first or second materials being connected can be provided in a form (e.g., in combination with an appropriate solution) that promotes their adhesion.

Figure 6D:
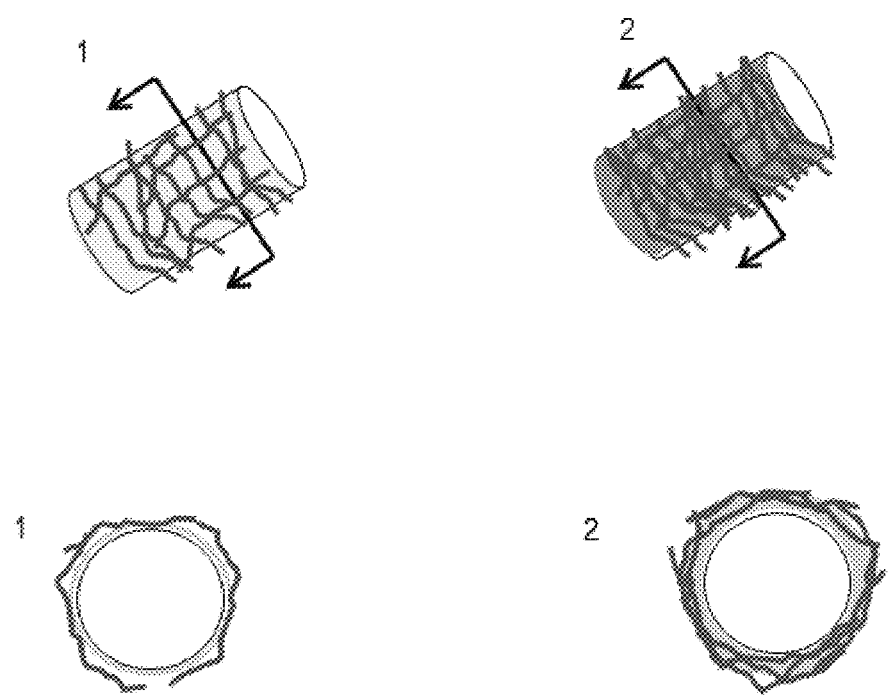
FIG. 6D illustrates a non-limiting example (right-hand panels) of a cross-section showing fibers that are deposited (e.g., by electrospinning) into a layer of dissolved material (e.g., polymer) of a scaffold component.

In some embodiments, the material (e.g., a polymer) for a scaffold component such as a support component, for example a rib of an airway scaffold, can be provided in combination with a solvent to generate a thicker layer of dissolved or melted (e.g., partially dissolved or partially melted) material that can be attached to fibers that are deposited onto the scaffold component (e.g., by electrospinning). FIG. 6D illustrates a non-limiting embodiment (right-hand panels) of a cross-section showing fibers that are deposited (e.g., by electrospinning) into a layer of dissolved material (e.g., polymer) of a scaffold component. The left-hand panel illustrates an example where less or no solvent is used or where only a small amount of solvent is deposited on the surface of the scaffold component. This illustrates that fewer fibers are tightly associated with the scaffold component in the left-hand panel. The thicker layer of dissolved material in the right-hand panel results in a thicker layer of material (e.g., polymer) for the fiber to get caught in. This results in a stronger attachment of fibers to the scaffold component and consequently a stronger scaffold that is less prone to delamination. In some embodiments, a scaffold component (e.g., a structural component) can be made using an electrospinning polymer solution that is less than 75% (e.g., about 70% or less, about 50% or less, or about 25% or less) polymer/solvent by volume. In some embodiments, a solvent includes or is HFIP. However, other solvents or combinations of solvents also may be used. In some embodiments, a polymer mixture for electrospinning is between about 50% PET and 100% PET. In some embodiments, the polymer mixture is 50% PET and 50% PU. In some embodiments, the polymer mixture is 100% PET. However, it should be appreciated that other polymer mixtures can be used.

In some embodiments, the physical integration of two or more different layers or components of a scaffold can be enhanced by depositing them and/or otherwise bringing them into contact before the material of one or both has set or cured. For example, a first material (e.g., a sheet or layer of a polymer, or a structural component) may be deposited and a second material (e.g., a sheet or layer of polymer, or a structural component) may be deposited on the first material before the first material has set or cured. This can be accomplished using any suitable technique. In some embodiments, the second material is applied rapidly before sufficient time has elapsed for the first material to set or cure. In some embodiments, the first material is provided as a dilute preparation or a wet preparation to slow down the process of setting or curing. In some embodiments, the first material is not exposed to curing or setting condition, agents, and/or stimulants prior to application of the second material. It should be appreciated that one or more of these techniques can be used and/or combined with other suitable techniques. In some embodiments, a series of different materials, layers, and/or components of a scaffold can be applied using these techniques alone or in combination with any other techniques described herein.

Figure 7A:
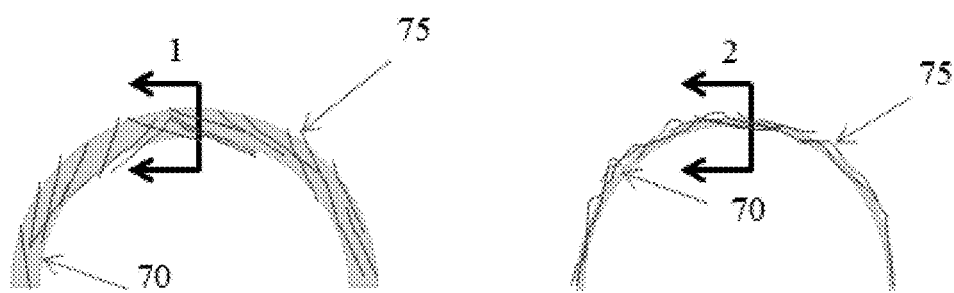
FIG. 7A illustrates side-views of different non-limiting examples of support structures (e.g., tracheal ribs) having different cross-sectional profiles.
Figure 7B:
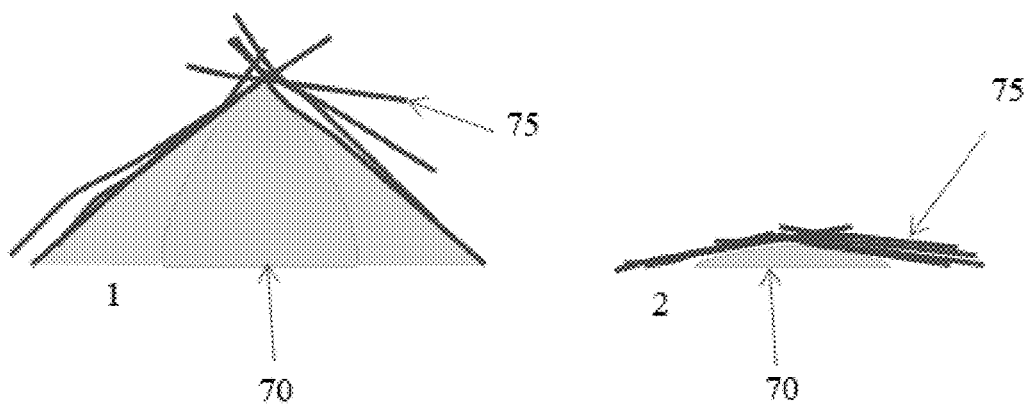
FIG. 7B illustrates the different cross-sectional profiles of support structures (e.g., tracheal ribs) of FIG. 7A.

In some embodiments, the size and shape of different scaffold components can be used to promote structural integrity. In some embodiments, the size and shape of a first structure (e.g., a support structure such as a synthetic tracheal ring or rib) can be optimized to promote adhesion of a second material to the first structure. For example, when an electrospun nanofiber is deposited onto a first structure (e.g., a support structure such as a synthetic tracheal ring or rib), adhesion between the two materials is enhanced when the first structure has a low profile (e.g., a low cross-sectional profile). By way of example, low profile structures include, but are not limited to, structures having flat or substantially flat surfaces, as well as structures having surface features, such cylindrical portions, rounded portions, or other shaped portions, in which the features have sufficiently large radii of curvature so as to facilitate or enable adhesion between two materials. In some embodiments, a structural component (e.g., a rib) that has a low cross-sectional profile is flatter or more ribbon-like than a structural component with a relatively higher cross-sectional profile. For example, FIG. 7 illustrates non-limiting embodiments of different cross-sectional profiles of a support structure (e.g., a rib of a tracheal scaffold or other scaffold). In FIG. 7A, support structure (70) is shown in side view with a higher profile in the left panel than in the right panel. FIG. 7B shows the relative cross-sectional profiles, with section 1 illustrated in the left panel and section 2 illustrated in the right panel. The feature (e.g., the structural rib) having a higher profile illustrated in the left panel provides less contact area between layers. In FIG. 7B, the extent of deposition of fibers 75 is lower on the flanking sides of the support structure (in the gray shadowed areas on either side of the structure in the left panel). In contrast, increased deposition is obtained on a support structure that has a lower cross-sectional profile (see right panel of FIG. 7B). As a result, the strength of the attachment between the nanofibers and the support structure is lower for the support structure illustrated in the left panel of FIGS. 7A and 7B. This can result in a higher risk for detachment or delamination. In some embodiments, a profile that promotes adhesion has a height:width ratio (of the cross-sectional profile) of less than 1:1 (e.g., between 1:1.1 and 1:10, for example around 1:1 and ⅓). Accordingly, the profile of a synthetic structure (e.g., a rib or ring or other support structure) that is being coated with fibers (e.g., electrospun nanofibers) can be designed to reduce the size of the gap between the fibers and the sides of the synthetic structure. This can increase the area of contact and adhesion between the fibers and the synthetic structure, thereby promoting structural integrity. In some embodiments, the surface texture of a synthetic structure also can be modified to promote adhesion with fibers that are being deposited. For example, notches, etches, or other surface depressions or protrusions, or a combination thereof, can be used to promote fiber attachment.

However, it should be appreciated that in some embodiments, the space between the structure and the second material (e.g., as illustrated in the gray flanking regions in the left panel of FIG. 7B) can be used (e.g., if the attachment strength is otherwise sufficient). For example, the space may be filled with a further material (e.g., a hormone, growth factor, or other material that may be useful to promote cell growth, differentiation, or other properties on a synthetic scaffold).

In some embodiments, a sheath is placed between a support (e.g., a mandrel) and a synthetic material (e.g., synthetic scaffold) that is being assembled or produced on the support (e.g., by electrospinning fibers onto the support). A sheath can be useful to prevent adhesion to the support by one or more of the materials (e.g., fibers) that is being deposited. In some embodiments, the sheath can be helpful to remove the support (e.g., mandrel) after assembly or synthesis of a synthetic scaffold is complete without significantly disrupting or damaging the integrity of the synthetic scaffold. In some embodiments, the sheath can then be removed from the synthetic scaffold by pealing it off or by stretching or otherwise deforming the sheath along one direction (e.g., the along the length of a tubular structure) such that the radius or width of the sheath shrinks thereby disconnecting it from the synthetic scaffold that is on the outer surface of the sheath.

In some embodiments, a sheath is designed to conform to the shape of the structure it is covering (e.g., a mandrel). In some embodiments, the sheath is an elastic or otherwise deformable structure. The sheath can be made of any suitable elastic, polymeric, and/or other synthetic or natural material. In some embodiments, the sheath includes one or more electrically conducting materials so that current can flow from/to the mandrel to allow fibers (e.g., nanofibers) to be electrospun onto the exposed surface of the sheath.

Figure 8A:
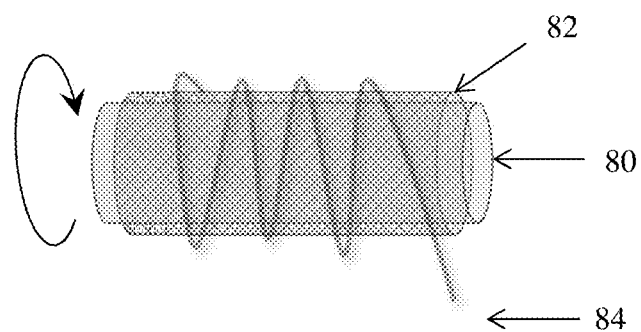
FIG. 8A illustrates a non-limiting example of a sheath on a cylindrical support, and fiber being deposited onto the sheath.
Figure 8B:
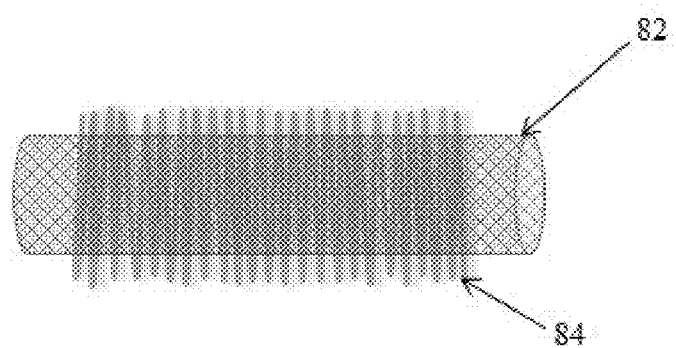
FIG. 8B illustrates a non-limiting example of the sheath inside a synthetic scaffold after removal of the support.

FIG. 8 illustrates a non-limiting example of a fiber (e.g., a macro or nanofiber) being deposited on a sheath. In FIG. 8A, sheath (82) is shown on a cylindrical support (e.g., a mandrel) (80), and fiber (84) is being deposited onto sheath (82). FIG. 8B illustrates the sheath inside a synthetic scaffold formed by fiber (84) after removal of support (80). The sheath is shown stretched so that its radius is reduced and it disconnects from the scaffold. It should be appreciated that support (80) can be a collector (e.g., a mandrel) or other structure that is used to form a scaffold but that is not integrated into the scaffold, and is removed from the scaffold prior to cellularization and/or prior to implantation.

A sheath can be made of or include a woven material and/or a polymer and/or any other suitable material. In some embodiments, a sheath is made of or includes one or more electrically conductive materials. Non-limiting examples of electrically conductive materials include, but are not limited to, conductive metals (e.g., silver, copper, annealed copper, gold, aluminum, calcium, tungsten, zinc, nickel, lithium, iron, platinum, tin, lead, titanium, manganin, constantan, mercury, nichrome, carbon (amorphous)); conductive plastics; conductive or anti-static powders/agents (e.g., the EP1/EP2/EP3/EP4 series available commercially from Noelson Chemicals); conductive glass powder (e.g., the EG series available commercially from Noelson Chemicals); conductive mica powder (e.g., the EC-300 series available commercially from Noelson Chemicals); conductive titanium dioxide (e.g., EC-320 series available commercially from Noelson Chemicals); conductive barium sulfate (e.g., the EC-340 series available commercially from Noelson Chemicals); conductive ATO powder (e.g., the EC-360 series available commercially from Noelson Chemicals); conductive zinc oxide (e.g., the EC-400 series available commercially from Noelson Chemicals); conductive polyaniline (e.g., the EC-600 series available commercially from Noelson Chemicals); conductive carbon or black/conductive graphite (e.g., the EC-380/EC-390 series available commercially from Noelson Chemicals); high conductive carbon powder (e.g., the EC series available commercially from Noelson Chemicals), and/or carbon nanotubes (e.g., the EC-700 series available commercially from Noelson Chemicals).

In some embodiments, one or more structural components (e.g., 2-20, 2-5, 5-10, 10-15, 15-20, or more) can be incorporated into a synthetic scaffold (e.g., onto a first layer of an electrospun scaffold) using a device that guides the placement of the support structure(s) without significantly disrupting or damaging the structure of the scaffold (e.g., of the first layer of the scaffold). In some embodiments, a device can be used to align and place a plurality of structural elements onto a synthetic scaffold during synthesis. In addition to reducing damage to an existing synthetic scaffold, the correct alignment of a plurality of structural elements can help promote the correct assembly of a complete scaffold and enhance the subsequent integrity of the scaffold (e.g., by reducing delamination or other structural failure of the assembled scaffold during or after implantation into a subject).

Figure 9A:
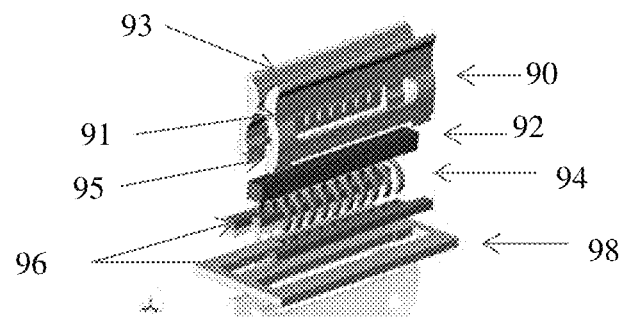
FIG. 9A illustrates a non-limiting example of a device that can be used to place one or more support rings onto a scaffold (e.g., a tubular scaffold), in which are shown spreader blocks inserted into a positioning frame.
Figure 9B:
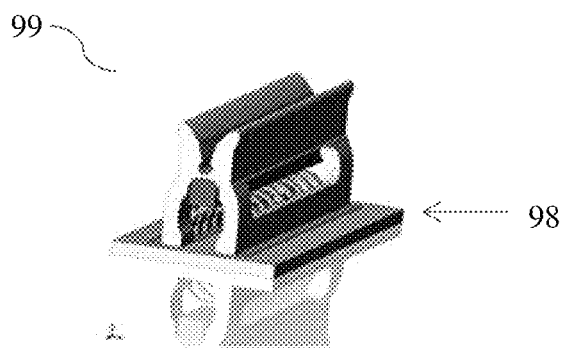
FIG. 9B illustrates a non-limiting example of two spreader blocks positioned in a positioning frame resulting in an assembled device for placing one or more support rings onto a scaffold.
Figure 9C:
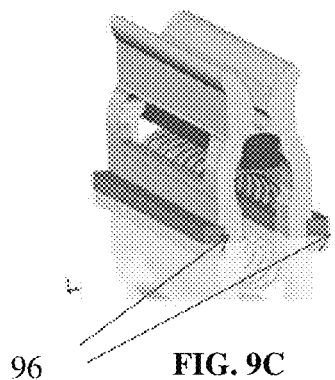
FIG. 9C illustrates a non-limiting example of two spreader blocks with a ring array being lifted out of a positioning frame without falling off the extension feet of the spreader.

FIG. 9 illustrates a non-limiting example of a device that can be used to place one or more support rings onto a scaffold (e.g., a cylindrical scaffold). In some embodiments, support rings are not closed circles, but are arcuate (e.g., U or C-shaped) open structures. In some embodiments, the ends of the U or C-shaped structures are in close proximity when the structure is not stretched or strained. However, the shape of the U or C-shaped structures and the distance between the ends of each structure depends on the intended use of the rings. In some embodiments, the rings (94) are used to provide a synthetic structural rib for a synthetic airway scaffold (e.g., a synthetic tracheal scaffold). In FIG. 9A, spreader blocks (96) are inserted into positioning frame (98). Synthetic rings (94) are inserted into pockets of spreader blocks (96). The pockets are at predetermined positions to align the rings (94). A pad (92) is fixed to the spreader (90) immediately below the flexible hinge (91) web. The pad (92) can be a silicone sponge rubber pad, or made of any other suitable material. The device is assembled with the rings (94) by lowering the spreader over rings such that the four extension feet slip downward into the matching cutouts at each end of each spreader block (96). As a result, the sponge rubber contacts the top of each ring (94) as the spreader extension feet (95) become fully inserted in the spreader blocks (96). In some embodiments, the two spreader blocks (96) can be positioned in a positioning frame (98) resulting in an assembled device (99) as illustrated in FIG. 9B. In some embodiments, by applying light pressure to the spreader handle (93) (e.g., by squeezing the sides of the spreader handle (93)) the two spreader blocks (96) with the ring array can be lifted out of the positioning frame (98) without falling off the four extension feet (95) of the spreader (90) (as illustrated in FIG. 9C). Squeezing the spreader (90) handles (93) further will separate the spreader blocks (96) (and spread the rings) such that the assembly may be placed over a mandrel to which a first layer of electrospun fiber has been applied. The assembled device (99) can be centered and lowered to bring the inside top of each ring in contact with the topside outer diameter of the electrospun fibers on the mandrel. In some embodiments, pressing the spreader (90) down further will cause the rings (94) to compress into the pad (92) (e.g., a pad made of silicone, a silicone sponge, or a rubber material, etc.). Since the spreader blocks (96) are held fixed by engagement with the four spreader extension feet (95), compressing the rings (94) into the silicone pad (92) effectively pulls each end of each ring (94) out of the pockets in the spreader blocks (96). As a result, the spreader blocks (96) can be released by all of the ring ends simultaneously, and the spreader blocks (96) can fall away or be removed from the spreader extension feet (95). When the spreader blocks (96) are released, the unconstrained rings (94) are free to snap back to their arcuate (e.g., circular) profile and wrap themselves around the electrospun fiber. Maintaining the pressure on the spreader handles (93) allows the spreader (93) to be lifted off the mandrel and ring assembly without disturbing the ring placement. In some embodiments, the resulting mandrel and ring assembly can be further processed by depositing a further layer of fibers (e.g., electrospun fibers) over the rings (94). It should be appreciated that the support components (e.g., rings) can have a size that is identical or similar to a tracheal or esophageal ring of a recipient of the scaffold. This size can be different depending on whether the recipient is a small mammal (e.g., a mouse), a human, or a larger mammal, or other organism. However, support components (e.g., ring or rib) can range in size from several mm (e.g., 1-2, 2-5, 5-10) to several cm (e.g., 1-2, 2-5, 5-10) inner diameter or smaller or larger. In some embodiments, the cross-sectional dimensions (e.g., width and height) of the support component can independently be around 1-10 mm or smaller or larger (e.g., 10-25 mm or larger).

It should be appreciated that one or more device components described herein may be optional and/or integral to an alignment device in some embodiments. It should be appreciated that an alignment device can be provided in different configurations that allow a plurality of structural elements (e.g., arcuate, or ring-shaped elements) to be placed onto a synthetic scaffold. It also should be appreciated that components of an alignment device can be made of any suitable material (e.g., including one or more plastics, metals, polymers, and/or other material, for example any suitable material that is autoclavable).

Figure 10:
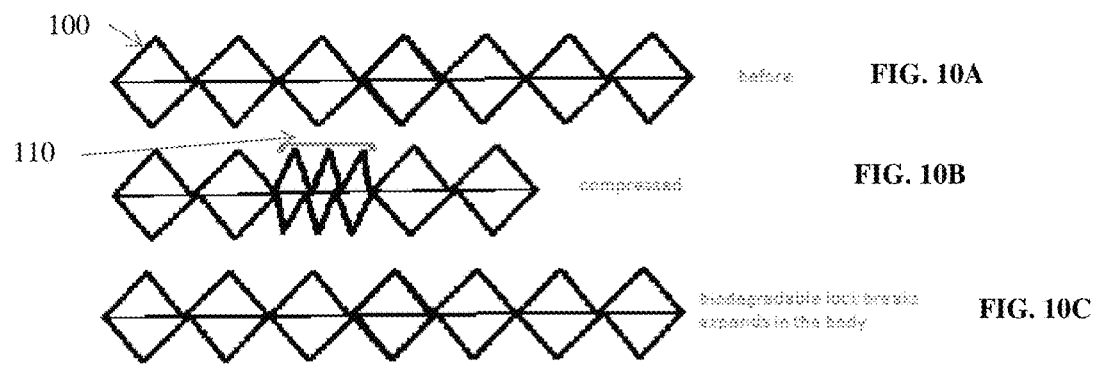
FIG. 10A illustrates a non-limiting embodiment of a scaffold having a plurality of compressible regions.
FIG. 10B illustrates a non-limiting example where three compressible regions are compressed and maintained in a compressed state by a lock.
FIG. 10C illustrates a non-limiting example where compressible regions expand when a biodegradable lock breaks.

In some embodiments, a scaffold may need to change size after implantation. For example, a scaffold implanted into a child or adolescent subject may need to expand in one or more directions as the subject grows. In some embodiments, a scaffold includes one or more expandable regions. In some embodiments, one or more regions are compressed prior to implantation and released after implantation (e.g., in response to one or more natural or added cues). FIG. 10 illustrates a non-limiting embodiment of a scaffold that can be compressed prior to implantation in a subject and subsequently extended after implantation. FIG. 10A illustrates a non-limiting embodiment of a scaffold having a plurality of compressible regions (100). FIG. 10B illustrates a non-limiting embodiment where 3 compressible regions are compressed and maintained in a compressed state by lock (110). In some embodiments, lock (110) is biodegradable and degrades after implantation thereby releasing the compressed regions and allowing the scaffold to expand. It should be appreciated that other locks can be used (e.g., ones that require an external cue or a physical intervention to be released at an appropriate time). In some embodiments, a compressed scaffold can be implanted without a lock. For example, in some embodiments, a compressed scaffold is maintained in a compressed state by the body of the subject at the site of implantation, but is slowly released as the body of the subject grows. It should be appreciated that the force required to compress the scaffold (and the resulting force that the compressed scaffold exerts on a body at the site of implantation) can be specified and be sufficiently low to prevent damage at the site of implantation by designing and producing a scaffold having suitable structural properties.

In some embodiments, a scaffold can include one or more regions having different elasticities, for example to allow more elastic regions to expand more readily, for example in daily use after implantation, and/or due to growth of the patient.

In some embodiments, the surface or a portion of the surface of a synthetic scaffold can be covered or strengthened in order to protect it after synthesis and before implantation. In some embodiments, one or more non-limiting techniques illustrated in FIG. 11 can be used to protect the surface of a synthetic scaffold. In some embodiments, it is beneficial to protect the scaffold surface to prevent damage or degradation (including delamination or partial delamination, loosening or other damage of fiber materials, deactivation of surface properties, etc., or any combination thereof) that could occur during manipulation of the scaffold (for example during cellularization or other procedures prior to implantation). In some embodiments, one or more techniques illustrated in FIG. 11 can be used to protect the surface of a scaffold from scratches, pulling, tearing, contamination, chemical spills, or other damage that can occur when the scaffold is touched or otherwise manipulated. This can be useful to maintain surface characteristics that promote cell adhesion or growth. It should be appreciated that techniques illustrated in FIG. 11 can be used with electrospun scaffolds and also with scaffolds produced using any other method (e.g., by molding, casting, printing, or lithography, or any combination thereof, including combinations with electro spinning).

Figure 11A:
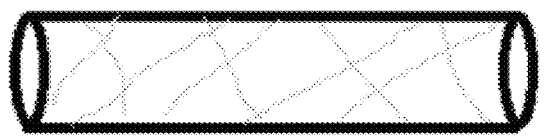
FIG. 11A illustrates a non-limiting example of a protective material (e.g., a durable fiber) spun or wrapped over a scaffold to cover a portion of the surface to reduce the surface area that is vulnerable to damage.
Figure 11B:
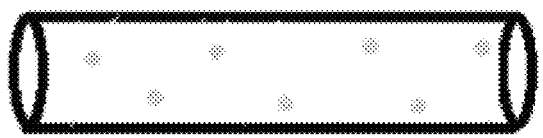
FIG. 11B illustrates a non-limiting example of a solubilizing or adhesive chemical and/or an adhesive material deposited in one or more regions to strengthen the connection between different fibers at the surface of a scaffold.
Figure 11C:
FIG. 11C illustrates a non-limiting example of a scaffold surface coated with a soluble material than can be dissolved and removed (e.g., washed away) when the scaffold is conditioned for use (e.g., for cellularization)
Figure 11D:
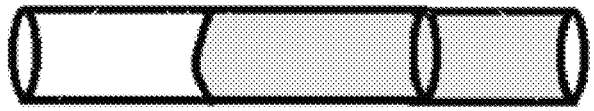
FIG. 11D illustrates a non-limiting example where a cover is applied to a scaffold.
Figure 11E:
FIG. 11E illustrates a non-limiting example of a cross-section of a portion of a scaffold showing protrusions or brushes on the side that is contacted when the scaffold is manipulated.

In FIG. 11A, a protective material (e.g., a durable fiber) is spun or wrapped over the scaffold to cover a portion of the surface to reduce the surface area that is vulnerable to damage. The material can be deposited in any suitable pattern. In FIG. 11B, a solubilizing or adhesive chemical (e.g., hexafluoroisopropanol, other hexanes, or other solvents or adhesives) and/or an adhesive material (e.g., fibrin or other adhesive material) is deposited (e.g., sprayed, painted, printed, dabbed, or otherwise deposited) in one or more regions to strengthen the connection between different fibers at the surface of the scaffold. It should be appreciated that the chemical or material can be deposited in any suitable pattern that does not interfere with subsequent uses (e.g., subsequent cellularization) as aspects of the disclosure are not limited in this respect. In FIG. 11C, a scaffold surface is coated with a soluble material than can be dissolved and removed (e.g., washed away) when the scaffold is conditioned for use (e.g., for cellularization). In some embodiments, the soluble material is a sugar. However, any suitable soluble material can be used as aspects of the invention are not limited in this respect. FIG. 11D illustrates a non-limiting embodiment where a cover is applied to the scaffold. The cover can include a pattern or design that provides a protective relief that reduces the exposure of the scaffold surface to potentially damaging contact. In some embodiments, a pattern of ridges, bumps, brushes, or other structures can be used to protect the scaffold surface from contact when the scaffold is manipulated. For example, the pattern can be designed such that the ridges, bumps, brushes, or other structures will be contacted when the scaffold is manipulated without the underlying surface being significantly damaged. FIG. 11E illustrates a non-limiting embodiment of a cross-section of a portion of a scaffold showing bumps or brushes on the side that is contacted when the scaffold is manipulated.

Figure 11F:
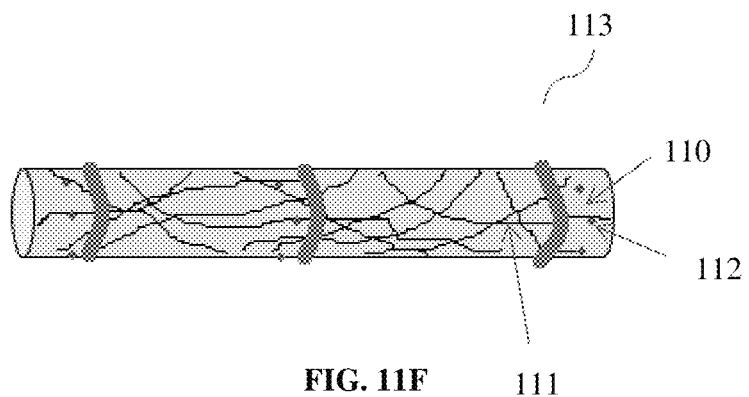
FIG. 11F illustrates a non-limiting example of spot-welds on a synthetic tissue scaffold.

In some embodiments, synthetic scaffolds are provided for growing tissues or organs. In some embodiments, fibers from different layers are attached together using physical techniques (e.g., sutures, welding, for example micro welding such as micro-ultrasound welding, or laser welding, or any other suitable form of welding) and/or chemical techniques (e.g., one or more solvents, cross-linking agents, etc., or any combination thereof). In some embodiments, physical welding (e.g., micro ultrasound or laser welding) may be used to attach together fibers from different layers of a synthetic scaffold. In some embodiments, different patterns can be used to weld multiple layers of fibers at a single point (e.g., a point of less than 1.8 mm in size). FIG. 11F illustrates a first layer (110) and a second layer (111) of a synthetic scaffold (113), in which welding (e.g., micro ultrasound or laser welding) has been used to create micro welds (112) that attach the second layer (111) (e.g., a layer of electrospun fibers) to the first layer (110) to form a synthetic scaffold (113). In this way, FIG. 11F illustrates a pattern of welds joining the first layer (110) and the second layer (111). Any suitable pattern of micro welds (112) may be used to join layers in a synthetic scaffold to eliminate delamination problems of the layers. For example, the weld patterns may be a point source, diamond shape, random or chaotic patterns or other suitable pattern. It should be appreciated that similar techniques can be used to connected other scaffold components (e.g., structural components) to each other or to one or more layers of material (e.g., electrospun material). In some embodiments, welding is only done on an edge or end of a mulitlayer scaffold. In some embodiments, welding at one or more ends or edges of a scaffold (e.g., at one or both ends of a tubular scaffold) has a pattern that is two-dimensional (e.g., a "W" pattern or other two-dimensional pattern) so that if a portion of the scaffold is removed (e.g., excised), for example to test one or more properties of a scaffold, or during surgical implantation, some of the welding remains with the scaffold that is being implanted (for example the excision of one or more ends or edges does not remove all of the welding).

Figure 11G:
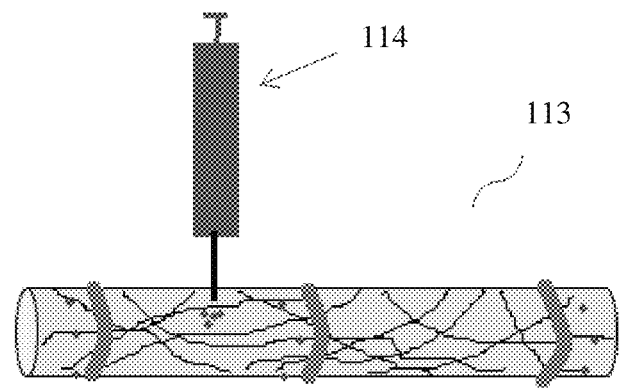
FIG. 11G illustrates a non-limiting example of solvents or adhesives being applied with a syringe to fibers of a synthetic tissue scaffold.

As depicted in FIG. 11G, in some embodiments, chemical solvents or adhesives or polymers (e.g., air or other curable setting polymers) that are capable of wetting surfaces or layers to fuse or adhere together can be added (e.g., by injection with a syringe or other delivery device (114)) during or after the fabrication process.

Figure 11H:
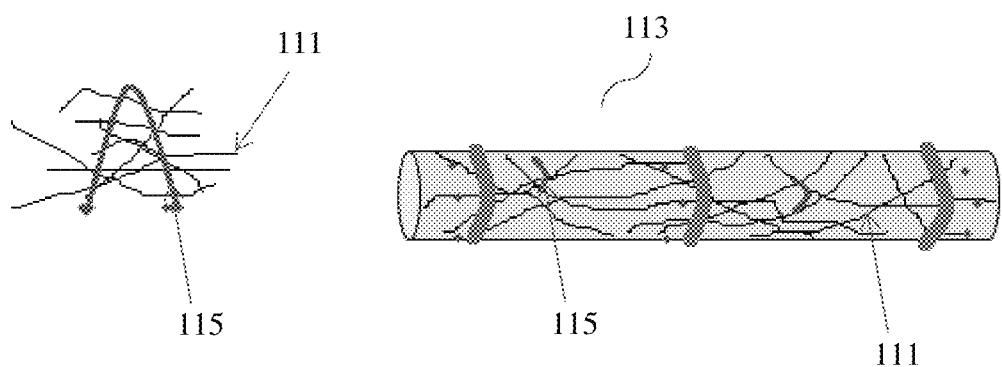
FIG. 11H illustrates a non-limiting example of a tethering element looped through fibers of a synthetic tissue scaffold.

As depicted in FIG. 11H in some embodiments, a string, suture or other fastening or tethering element (115) can be looped through fibers (111) and secured at one or more ends of a synthetic scaffold (113). In some embodiments, the string, suture or other fastening element may be secured by melting a knot or placement of a chemical dot such that the string or suture remains fixed at the end and does not unravel, for example. In some embodiments, the string, suture or other fastening element is a natural fiber (e.g., a silk fiber). In some embodiments, the string, suture or other fastening element is a synthetic fiber (e.g., a nylon fiber). In some embodiments, the string, suture or other fastening element is biodegradable and/or biocompatible. It should be appreciated that any of these techniques can be used independently or together.

It should be appreciated that these techniques can be used to assemble unique organ features, for example, by establishing for an organ a structure and using the methods to bind layers of material together, as well as in some embodiments to build micro or macro features of an organ. For example, in some embodiments, a synthetic organ with kidney function may be constructed that has a well or channel or other cavity made for nephrons by bending a polymer sheet and using one of the attachment techniques disclosed herein to fuse or connect the pieces together. In some embodiments, the methods may be applied for synthetic organ fabrication. In some embodiments, the attachment methods may be applied for adding (or attaching) synthetic components of an organ to natural organs, for example, where there may be a section of an natural organ that is to be reconstructed.

Scaffold Properties

It should be appreciated that aspects of the invention are useful for enhancing the stability and/or structural integrity of any scaffold, for example a scaffold based on electrospun fibers.

In some embodiments, one or more scaffold components can be thin sheets, cylinders, thick ribs, solid blocks, branched networks, etc., or any combination thereof having different dimensions. In some embodiments, the dimensions of a complete and/or assembled scaffold are similar or identical to the dimension of a tissue or organ being replaced. In some embodiments, individual components or layers of a scaffold have smaller dimensions. For example, the thickness of a nanofiber layer can be from several nm to 100 nm, to 1-1000 microns, or even several mm. However, in some embodiments, the dimensions of one or more scaffold components can be from about 1 mm to 50 cms. However, larger, smaller, or intermediate sized structures may be made as described herein.

In some embodiments, scaffolds are formed as tubular structures that can be seeded with cells to form tubular tissue regions (e.g., tracheal, bronchial, or other tubular regions). It should be appreciated that a tubular region can be a cylinder with a uniform diameter. However, in some embodiments, a tubular region can have any appropriate tubular shape (for example, including portions with different diameters along the length of the tubular region). A tubular region also can include a branch or a series of branches. In some embodiments, a tubular scaffold is produced having an opening at one end, both ends, or a plurality of ends (e.g., in the case of a branched scaffold). However, a tubular scaffold may be closed at one, both, or all ends, as aspects of the invention are not limited in this respect. It also should be appreciated that aspects of the invention may be used to produce scaffolds for any type or organ, including hollow and solid organs, as the invention is not limited in this respect. In some embodiments, aspects of the invention are useful to enhance the stability of scaffold or other structures that include two or more regions or layers of fibers (e.g., electrospun nanofibers) that are not physically connected.

In some embodiments, a scaffold is designed to have a porous surface having pores ranging from around 10 nm to about 100 micron in diameter that can promote cellularization. However, it should be appreciated that pores of other sizes also can be included. In some embodiments, a surface layer of a scaffold is synthesized using fibers that include one or more dissolvable particles that can be dissolved during or after synthesis (e.g., by exposure to a solvent, an aqueous solution, for example, water or a buffer) to leave behind pores the size of the dissolvable particles. In some embodiments, the particles are included in the polymer mix that is pumped to the nozzle of an electrospinning device. As a result the particles are deposited along with the fibers. In some embodiments, the electrospinning procedure is configured to deposit thick fibers (e.g., having an average diameter of several microns, about 10 microns, and thicker). In some embodiments, if the fibers are deposited in a dense pattern, one or more fibers will merge prior to curing to form larger macrostructures (e.g., 10-100 microns thick or more). In some embodiments, these macrostructures can entangle two or more layers of fibers and or portions (e.g., fibers) from two or more different components of a scaffold thereby increasing the mechanical integrity of the scaffold. In some embodiments, when such macrostructures are formed (e.g., via electrospinning as described herein) at one or more stages during scaffold synthesis (e.g., to connect two or more layers and/or components), the surface of the macrostructure(s) can be treated (e.g., etched or made porous using dissolvable particles as described herein) in order to provide a surface suitable for cellularization.

In some embodiments, one or more components of a scaffold (e.g., a structural component such as a rib or a single continuous support structure) can function as a delivery device for a drug or other compound. In some embodiments, the one or more components can be coated and/or include one or more reservoirs of a drug or other compound (e.g., one or more growth factors that promote cell growth and/or differentiation, a therapeutic drug or compound, an immunomodulatory drug or compound, a drug or compound that acts on the scaffold or a portion thereof, a drug or compound that acts on the circulatory system of the host, a drug or compound that promotes vascularization and or other tissue growth in the host, or other drug or compound, or any combination thereof).

In some embodiments, a drug or compound is delivered by elution from a coating, impregnation, or surface treatment of a scaffold component. In some embodiments, a drug or compound is delivered by liquid injection from a reservoir within a scaffold component. In some embodiments, a drug or compound is delivered from one or more reservoirs (e.g., bladders) in a scaffold component. It should be appreciated that the one or more reservoirs can deliver similar or different volumes of one or more different drugs or compounds. In some embodiments, a drug or compound is delivered by immediate release, delayed release, extended release, or a combination thereof.

In some embodiments, the amount of flexible scaffold material (e.g., the slack) between two or more structural components (e.g., rings) or between structural members (e.g., arcuate members) of a single continuous structural component can be used to determine the mechanical properties (e.g., tensile strength, elongation, rotation, compression, range of motion, bending, resistance, compliance, degrees of freedom, elasticity, or any other mechanical property, or a combination thereof) of a complete synthetic tissue or organ structure.

In some embodiments, a frame (e.g., a single continuous structure as described herein) or a portion thereof, is maintained under stress (e.g., tensional, elongation, rotational, or other stress, or any combination thereof) as one or more scaffold layers are applied (e.g., via electrospinning). It should be appreciated that subsequent release or other modulation of these properties at the end of the fabrication process can determine the final amount of material between structural elements and thus the final mechanical properties. In some embodiments, the types and/or amount of stress that is applied can be adjusted (e.g., dynamically) during fabrication of a scaffold. In some embodiments, one or more adjustments are computer controlled (e.g., based on data collected about the scaffold during the fabrication process).

Support/Mandrel

In some embodiments, a scaffold (e.g., a scaffold having two or more layers) can be produced using a support (e.g., a solid or hollow support) on which the scaffold can be formed. For example, a support can be an electro spinning collector, for example a mandrel, or a tube, or any other shaped support. It should be appreciated that the support can have any size or shape. However, in some embodiments, the size and shape of the support is designed to produce a scaffold that will support an artificial tissue of the same or similar size as the tissue being replaced or supplemented in a host (e.g., trachea or other airway portion, blood vessel, liver or kidney region, or other tissue or organ). It should be appreciated that a mandrel for electrospinning should have a conductive surface. In some embodiments, an electrospinning mandrel is made of a conductive material (e.g., including one or more metals). However, in some embodiments, an electrospinning mandrel includes a conductive coating (e.g., including one or more metals) covering a non-conductive central support. In some embodiments, the surface of an electrospinning mandrel includes a pattern of different levels of conductivity (e.g., due to a pattern of different amounts of one or more metals on the surface of the mandrel). This can be used to produce a pattern of different amounts of fiber deposition (with more fiber being deposited on regions of higher conductivity). In some embodiments, the surface conductivity of a mandrel can be adjusted to produce different patterns for different applications. By altering the amount of fiber that is deposited in different areas on the mandrel, a pattern of different thicknesses can be produced without requiring separate layers or components to be connected to form a desired three dimensional scaffold having an appropriate pattern of thin and thick regions (e.g., corresponding to different functional and structural requirements for a scaffold).

Fibers

In some embodiments, scaffolds comprise one or more types of fiber (e.g., nanofibers). In some embodiments, scaffolds comprise one or more natural fibers, one or more synthetic fibers, one or more polymers, or any combination thereof. It should be appreciated that different material (e.g., different fibers) can be used in methods and compositions described herein. In some embodiments, the material is biocompatible so that it can support cell growth. In some embodiments, the material is permanent (e.g., PET), semi-permanent (e.g., it persists for several years after implantation into the host, or rapidly degradable (e.g., it is resorbed within several months after implantation into the host).

In some embodiments, the scaffold contains or consists of electrospun material (e.g. macro or nanofibers). In some embodiments, the electrospun material contains or consists of PET (polyethylene terephthalate (sometimes written poly(ethylene terephthalate)). PET is a thermoplastic polymer resin of the polyester family. PET consists of polymerized units of the monomer ethylene terephthalate, with repeating C10H8O4 units. Depending on its processing and thermal history, polyethylene terephthalate may exist both as an amorphous (transparent) and as a semi-crystalline polymer. The semicrystalline material might appear transparent (particle size <500 nm) or opaque and white (particle size up to a few microns) depending on its crystal structure and particle size. Its monomer (bis-β-hydroxyterephthalate) can be synthesized by the esterification reaction between terephthalic acid and ethylene glycol with water as a byproduct, or by transesterification reaction between ethylene glycol and dimethyl terephthalate with methanol as a byproduct. Polymerization is through a polycondensation reaction of the monomers (done immediately after esterification/transesterification) with water as the byproduct. In some embodiments, the electrospun material contains or consists of polyurethane (PU). In some embodiments, the electrospun material contains or consists of PET and PU.

In some embodiments, the artificial scaffold may consist of or include one or more of any of the following materials: elastic polymers (e.g., one or more polyurethanes (PU), for example polycarbonates and/or polyesters), acrylamide polymers, Nylon, resorbable materials (e.g., PLGA, PLA, PGA, PCL), synthetic or natural materials (e.g., silk, elastin, collagen, carbon, gelatin, chitosan, hyaluronic acid, etc.) or any combination thereof. In some embodiments, the scaffold may consist of or include addition polymer and/or condensation polymer materials such as polyolefin, polyacetal, polyamide, polyester, cellulose ether and ester, polyalkylene sulfide, polyarylene oxide, polysulfone, modified polysulfone polymers and mixtures thereof. In some embodiments, the scaffold may consist of or include polyethylene, polypropylene, poly(vinylchloride), polymethylmethacrylate (and other acrylic resins), polystyrene, and copolymers thereof (including ABA type block copolymers), poly(vinylidene fluoride), poly(vinylidene chloride), polyvinylalcohol in various degrees of hydrolysis (e.g., 87% to 99.5%) in cross-linked and non-cross-linked forms. In some embodiments, the scaffold may consist of or include block copolymers. In some embodiments, addition polymers like polyvinylidene fluoride, syndiotactic polystyrene, copolymer of vinylidene fluoride and hexafluoropropylene, polyvinyl alcohol, polyvinyl acetate, amorphous addition polymers, such as poly(acrylonitrile) and its copolymers with acrylic acid and methacrylates, polystyrene, poly(vinyl chloride) and its various copolymers, poly(methyl methacrylate) and its various copolymers, and PET (polyethylene terephthalate (sometimes written poly(ethylene terephthalate))) can be solution spun or electrospun and combined with any other material disclosed herein to produce a scaffold. In some embodiments, highly crystalline polymers like polyethylene and polypropylene may be solution spun or combined with any other material disclosed herein to produce a scaffold.

Electrospinning

In some embodiments, aspects of the invention relate to structures that are produced via electrospinning. Electrospun material can be used for a variety of applications, including as a scaffold for tissue engineering. Methods of electrospinning polymers are known in the art (see, e.g. (Doshi and Reneker. Electrospinning process and application of electrospun fibers. J. Electrostat. 1995; 35:151-60; Reneker D H, Chun I. Nanometer diameter fibers of polymer produced by electrospinning. Nanotechnology. 1996; 7:216-23; Dzenis Y. Spinning continuous fibers for nanotechnology. Science. 2004; 304:1917-19; or Vasita and Katti. Nanofibers and their applications in tissue engineering. Int J. Nanomedicine. 2006; 1(1): 15-30). Electrospinning is a versatile technique that can be used to produce either randomly oriented or aligned fibers with essentially any chemistry and diameters ranging from nm scale (e.g., around 15 nm) to micron scale (e.g., around 10 microns).

In some embodiments, electrospinning and electrospraying techniques used herein involve using a high voltage electric field to charge a polymer solution (or melt) that is delivered through a nozzle (e.g., as a jet of polymer solution) and deposited on a target surface. The target surface can be the surface of a static plate, a rotating drum (e.g., mandrel), or other form of collector surface that is both electrically conductive and electrically grounded so that the charged polymer solution is drawn towards the surface.

In some embodiments, the electric field employed is typically on the order of several kV, and the distance between the nozzle and the target surface is usually several cm or more. The solvent of the polymer solution evaporates (at least partially) between leaving the nozzle and reaching the target surface. This results in the deposition of polymer fibers on the surface. Typical fiber diameters range from several nanometers to several microns. The relative orientation of the fibers can be affected by the movement of the target surface relative to the nozzle. For example, if the target surface is the surface of a rotating mandrel, the fibers will align (at least partially) on the surface in the direction of rotation. In some cases, the nozzle can be scanned back and forth between both ends of a rotating mandrel. This can produce a mesh of fibers that forms a cylinder covering at least a portion of the surface of the mandrel.

In some embodiments, the size and density of the polymer fibers, the extent of fiber alignment, and other physical characteristics of an electrospun material can be impacted by factors including, but not limited to, the nature of the polymer solution, the size of the nozzle, the electrical field, the distance between the nozzle and the target surface, the properties of the target surface, the relative movement (e.g., distance and/or speed) between the nozzle and the target surface, and other factors that can affect solvent evaporation and polymer deposition.

Having thus described several embodiments with respect to aspects of the inventions, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

What is claimed is:

1. A method of enhancing the mechanical properties of a synthetic or natural tubular organ scaffold, the method comprising:

integrating one or more support structures that are electrically conductive within a tubular structure, wherein the support structure is a coiled structure and wherein the support structure is captured within an electrospun nanofiber structure, wherein the tubular organ scaffold has two or more layers of electrospun polymeric nanofiber wherein the electrospun polymeric nanofiber is polyethylene, polypropylene or a mixture of polyethylene and polypropylene, and wherein the support structure includes a plurality of anchors, the anchors having a diameter between 1 and 5 nm and a length between 5 and 50 nm; and seeding the scaffold with cells.

2. The method of claim 1, wherein the one or more support structures is a continuous support structure.

3. The method of claim 1, further comprising applying an electric charge or current to the support structure.

4. The method of claim 3, wherein the electric charge or current is applied to the support structure during synthesis of the scaffold.

5. The method of claim 3, wherein the charge is selectively controlled to alter the bonding properties of electrospun nanofiber layers.

6. The method of claim 1, wherein the support structure is integrated within the scaffold by electrospraying.

7. The method of claim 1, wherein the support structure is a ring or rib.

8. The method of claim 1, wherein the support structure comprises a metal.

9. The method of claim 1, wherein the support structure is sufficiently electrically conductive to permit heating of the support structure by applying an electric charge or current to permit melting of one or more layers of the tubular structure.

10. A method of enhancing the mechanical properties of a synthetic trachea scaffold comprising an electrospun nanofiber structure, the method comprising:

integrating a continuous coiled metallic support structure that is electrically conductive within the electrospun nanofiber structure of the synthetic trachea scaffold wherein the continuous coiled metallic support structure includes a plurality of anchors, the anchors having a diameter between 1 and 5 nm and a length between 5 and 50 nm;

heating the metallic support structure to melt one or more layers of the electrospun nanofiber structure; and
seeding the scaffold with cells.

11. The method of claim 10, wherein the metallic support structure is heated by applying an electric charge or current.

12. The method of claim 10, further comprising;
applying a protective material to a surface of the synthetic trachea scaffold.

13. The method of claim 12, wherein the protective material is a durable fiber, a solvent, an adhesive, or a soluble material.

14. The method of claim 12, wherein the protective material is applied in a predetermined pattern.

15. The method of claim 12, wherein the surface material provides a pattern of protective relief.

16. The method of claim 10, further comprising seeding the synthetic trachea, scaffold with cells.

* * * * *